United States Patent
Weaver et al.

(10) Patent No.: US 12,390,558 B2
(45) Date of Patent: Aug. 19, 2025

(54) INJECTION MOLDING TO GENERATE COMPLEX HYDROGEL GEOMETRIES FOR CELL ENCAPSULATION

(71) Applicants: Jessica Weaver, Tempe, AZ (US); Alec McCall, Tempe, AZ (US); Sarah Brady, Tempe, AZ (US)

(72) Inventors: Jessica Weaver, Tempe, AZ (US); Alec McCall, Tempe, AZ (US); Sarah Brady, Tempe, AZ (US)

(73) Assignee: Arizona Board of Regents on Behalf of Arizona State University, Tempe, AZ (US)

( * ) Notice: Subject to any disclaimer, the term of this patent is extended or adjusted under 35 U.S.C. 154(b) by 491 days.

(21) Appl. No.: 16/951,452

(22) Filed: Nov. 18, 2020

(65) Prior Publication Data
US 2021/0146010 A1 May 20, 2021

Related U.S. Application Data

(60) Provisional application No. 62/938,074, filed on Nov. 20, 2019.

(51) Int. Cl.
| | |
|---|---|
| A61L 27/18 | (2006.01) |
| A61L 27/38 | (2006.01) |
| A61L 27/52 | (2006.01) |
| A61L 27/54 | (2006.01) |
| B29C 33/42 | (2006.01) |
| B29C 45/03 | (2006.01) |
| B29C 45/26 | (2006.01) |
| B29C 45/64 | (2006.01) |
| C12N 5/00 | (2006.01) |
| C12N 5/071 | (2010.01) |
| B29C 45/00 | (2006.01) |
| B29K 105/00 | (2006.01) |
| B29L 31/00 | (2006.01) |

(52) U.S. Cl.
CPC ............ *A61L 27/52* (2013.01); *A61L 27/18* (2013.01); *A61L 27/3804* (2013.01); *A61L 27/54* (2013.01); *B29C 33/42* (2013.01); *B29C 45/03* (2013.01); *B29C 45/26* (2013.01); *B29C 45/64* (2013.01); *C12N 5/0012* (2013.01); *C12N 5/0676* (2013.01); *C12N 5/0677* (2013.01); *A61L 2300/62* (2013.01); *A61L 2300/64* (2013.01); *B29C 2045/0094* (2013.01); *B29K 2105/0061* (2013.01); *B29L 2031/753* (2013.01); *C12N 2533/30* (2013.01); *C12N 2533/74* (2013.01); *C12N 2533/76* (2013.01); *C12N 2535/00* (2013.01); *C12N 2537/10* (2013.01)

(58) Field of Classification Search
CPC ...... A61L 27/52; A61L 27/18; A61L 27/3804; A61L 2300/64; C12N 5/0012; C12N 5/0676; C12N 5/0677; C12N 2533/30; C12N 2535/00
See application file for complete search history.

(56) References Cited

U.S. PATENT DOCUMENTS

| | | | | |
|---|---|---|---|---|
| 5,410,016 A | * | 4/1995 | Hubbell | C12N 11/04 525/413 |
| 2002/0159982 A1 | * | 10/2002 | Bonassar | A61L 27/3886 435/325 |

OTHER PUBLICATIONS

Rios et al., Mold-casted non-degradable, islet macro-encapsulating hydrogel devices for restoration of normoglycemia in diabetic mice. Biotechnology and Bioengineering, vol. 113, No. 11 (Nov. 2016) pp. 2485-2495. (Year: 2016).*
Koh et al., (2003) Molding of hydrogel microstructures to create multiphenotype cell microarrays. Anal.Chem. 75(21): 5783-5789 (Year: 2019).*
Hunckler et al., Linkage groups within Thiol-ene photoclickable PEG hydrogels control in vivo stability. Advanced Healthcare Materials. vol. 8, No. 14 (Jul. 25, 2019) 1900371 (Year: 2019).*
Robles et al., Current status of islet encapsulation. Cell Transplantation, vol. 12, No. 11 (2014) pp. 1321-1348 (Year: 2014).*
Addington, et al., Siloxane Nanoprobes for Labeling and Dual Modality Functional Imaging of Neural Stem Cells. Ann Biomed Eng. 2016;44(3):816-27.
Balamurugan, et al., Bioartificial pancreas transplantation at prevascularized intermuscular space: effect of angiogenesis induction on islet survival. Pancreas. 2003;26(3):279-85.
Beck, et al., Islet encapsulation: strategies to enhance islet cell functions. Tissue engineering. 2007;13(3):589-99.
Buchwald, et al., Experimental evaluation and computational modeling of the effects of encapsulation on the time-profile of glucose-stimulated insulin release of pancreatic islets.
Clayton, et al., Islet microencapsulation: a review. Acta diabetologica. 1993;30(4):181-9.
Davies, et al., The dosage dependence of VEGF stimulation on scaffold neovascularisation. Biomaterials. 2008;29(26):3531-8.
deVos, et al., Alginate-based microcapsules for immunoisolation of pancreatic islets. Biomaterials. 2006;27 (32):5603-17.
Dionne, et al., Effect of hypoxia on insulin secretion by isolated rat and canine islets of Langerhans. Diabetes. 1993;42(1):12-21.
Dionne, et al., Effect of oxygen on isolated pancreatic tissue. ASAIO Trans. 1989;35(3):739-741.
Gulaka, et al., Hexamethyldisiloxane-based nanoprobes for 1H MRI oximetry. NMR Biomed. 2011;24(10):1226-34.

(Continued)

*Primary Examiner* — Kara D Johnson
(74) *Attorney, Agent, or Firm* — Polsinelli PC

(57) ABSTRACT

Provided herein is a cell macroencapsulation device composed of hydrogel in a 3D conformation that optimizes encapsulated cell viability and function when transplanted into a vascularized tissue space. The hydrogel macroencapsulation device is intended to reduce or eliminate immune response to the cell graft, while allowing exchange of encapsulated cell-secreted products, such as insulin. Also described herein is an injection-mold and fabrication process to generate the hydrogel macroencapsulation devices for use in the clinic.

11 Claims, 43 Drawing Sheets

(56) References Cited

OTHER PUBLICATIONS

Headen, et al., Local immunomodulation with Fas ligand-engineered biomaterials achieves allogeneic islet graft acceptance. Nat Mater. 2018;17(8):732-9. doi: 10.1038/s41563-018-0099-0. PubMed PMID: 29867165; PMCID: PMC6060019.
Jacobs-Tulleneers-Thevissen, et al., Sustained function of alginate-encapsulated human islet cell implants in the peritoneal cavity of mice leading to a pilot study in a type 1 diabetic patient. Diabetologia. 2013;56(7): p. 1605-1614.
Juang, et al., Outcome Of Subcutaneous Islet Transplantation Improved By Polymer Device1. Transplantation. 1996;61(11): p. 1557-1561.
Kodibagkar, et al., Novel 1H NMR approach to quantitative tissue oximetry using hexamethyldisiloxane. Magnetic Resonance in Medicine: An Official Journal of the International Society for Magnetic Resonance in Medicine. 2006;55(4):743-8.
Kodibagkar, et al., Proton imaging of siloxanes to map tissue oxygenation levels (PISTOL): a tool for quantitative tissue oximetry. NMR in Biomedicine: An International Journal Devoted to the Development and Application of Magnetic Resonance In vivo. 2008;21(8):899-907.
Komatsu, et al., Oxygen environment and islet size are the primary limiting factors of isolated pancreatic islet survival. PLoS One. 2017;12(8):e0183780.
Ludwig, et al., Transplantation of human islets without immunosuppre ssion. Proceedings of the National Academy of Sciences. 2013;110(47):19054-19058.
McKay, et al., Click chemistry in complex mixtures: bioorthogonal bioconjugation. 2014. 21(9): p. 1075-1101.
Menon, et al., Dual-modality, dual-functional nanoprobes for cellular and molecular imaging. Theranostics. 2012;2(12):1199.
Moulisouva, Engineered microenvironments for synergistic VEGF—Integrin signalling during vascularization. Biomaterials. May 2017; 126:61-74.
Navarro-Requena, et al., PEG hydrogel containing calcium-releasing particles and mesenchymal stromal cells promote vessel maturation. Acta Biomaterialia. Feb. 2018; 67:53-65.
Orive, et al., History, challenges and perspectives of cell microencapsulation. TRENDS in Biotechnology. 2004;22(2):87-92.
Pedraza, et al., Preventing hypoxia-induced cell death in beta cells and islets via hydrolytically activated, oxygen-generating biomaterials. Proceedings of the National Academy of Sciences. 2012;109(11):4245-50.
Pileggi, et al., Reversal of diabetes by pancreatic islet transplantation into a subcutaneous, neovascularized device. Transplantation. 2006;81(9):1318-24.
Reid, et al., PEG hydrogel degradation and the role of the surrounding tissue environment. 2015. 9(3): p. 315-318.

Ricordi, et al., Clinical islet transplantation: advances and immunological challenges. Nature Reviews Immunology. 2004;4(4):259-68.
Ryan, et al., Five-year follow-up after clinical islet transplantation. Diabetes. 2005;54(7):2060-9.
Sakurai, et al., The efficient prevascularization induced by fibroblast growth factor 2 with a collagen-coated device improves the cell survival of a bioartificial pancreas. Pancreas. 2004;28(3):e70-e9.
Sato, et al., Cellular hypoxia of pancreatic n-cells due to high levels of oxygen consumption for insulin secretion in vitro. J Biol Chem. 2011;286(14):12524-12532.
Shapiro AJ, Ricordi C, Hering BJ, Auchinclo ss H, Lindblad R, Robertson RP, Secchi A, Brendel MD, Berney T, Brennan DC. International trial of the Edmonton protocol for islet transplantation. New England Journal of Medicine. 2006;355(13):1318-30.
Skrzypek, et al., Pancreatic islet macroencapsulation using microwell porous membranes. Sci Rep. 2017;7(1):9186.
Suzuki, et al., Function and survival of macroencapsulated syngeneic islets transplanted into streptozotocin-diabetic mice. Transplantation. 1998;66(1):21-28.
Trivedi, et al., Improved vascularization of planar membrane diffusion devices following continuous infusion of vascular endothelial growth factor. Cell Transplant. 2000;9(1):115-24.
Tuch, et al., Safety and viability of microencapsulated human islets transplanted into diabetic humans. Diabetes Care. 2009;32(10):1887-9.
Veiseh, et al., Size-and shape-dependent foreign body immune response to materials implanted in rodents and non-human primates. 2015. 14(6): p. 643.
Wang, et al., Subcutaneous transplantation of macroencapsulated porcine pancreatic endocrine cells normalizes hyperglycemia in diabetic mice1. Transplantation. 2003;76(2):290-296.
Weaver, et al., Vasculogenic hydrogel enhances islet survival, engraftment, and function in leading extrahepatic sites. Science Advances. 2017;3(6):e1700184.
Weaver, et al., Synthetic poly(ethylene glycol)-based microfluidic islet encapsulation reduces graft vol. for delivery to highly vascularized and retrievable transplant site. Am J Transplant. 2018. doi: 10.1111/ajt.15168. PubMed PMID: 30378751.
Weaver, et al., Design of a vascularized synthetic poly (ethylene glycol) macroencapsulation device for islet transplantation. Biomaterials. 2018;172:54-65.
Weaver, et al., Controlled release of dexamethasone from organosilicone constructs for local modulation of inflammation in islet transplantation. Tissue Engineering Part A. 2015;21(15-16):2250-61.
Weaver, et al., Antioxidant cerium oxide nanoparticle hydrogels for cellular encapsulation. Acta biomaterialia. 2015;16:136-44.
Weir, Islet encapsulation: advances and obstacles. Diabetologia. 2013;56(7):1458-1461.

* cited by examiner

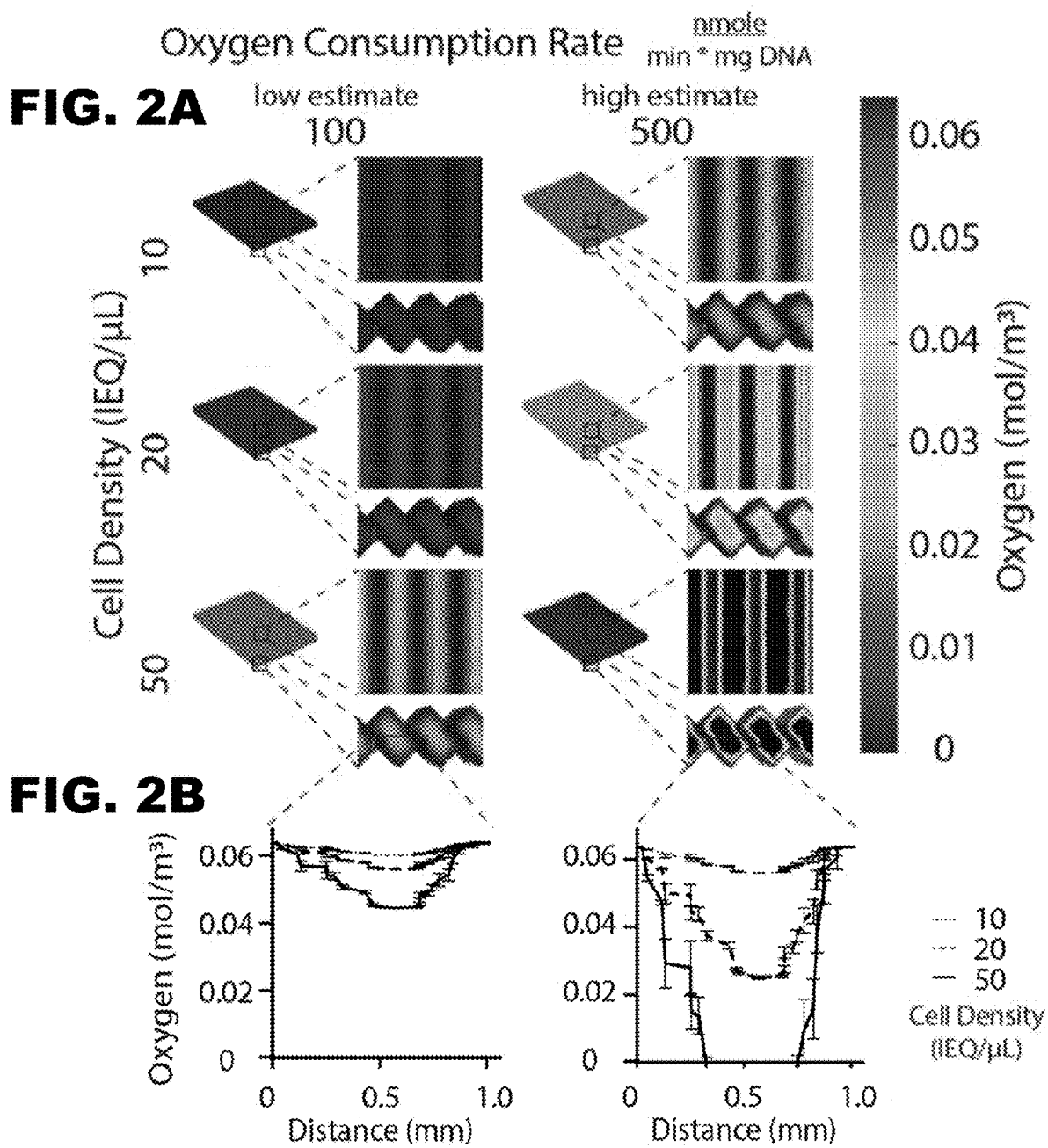

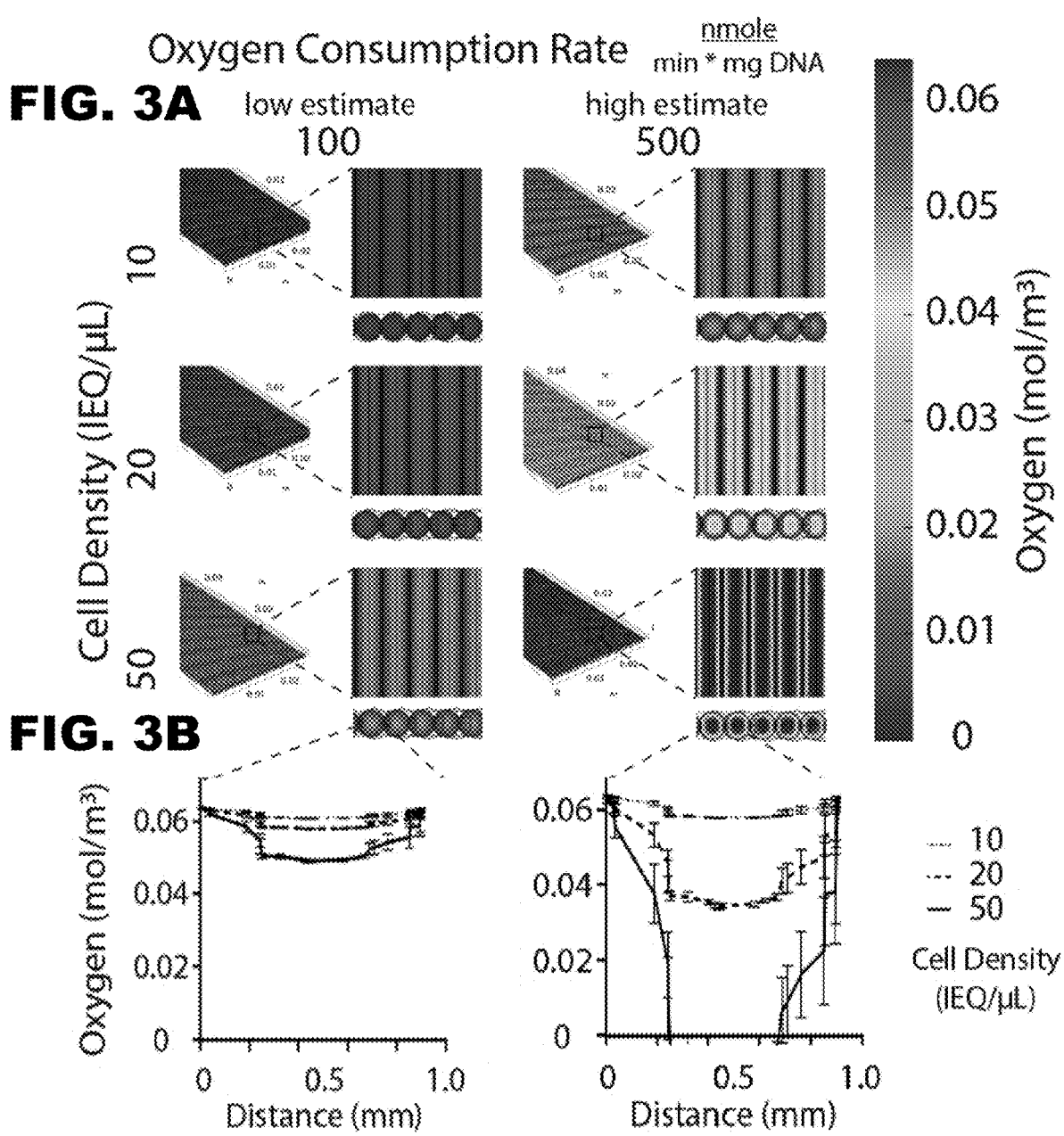

INJECTION MOLDING TO GENERATE COMPLEX HYDROGEL GEOMETRIES FOR CELL ENCAPSULATION

CROSS-REFERENCE TO RELATED APPLICATIONS

This application claims priority under 35 USC § 119(e) to U.S. Patent Application Ser. No. 62/938,074, filed on Nov. 20, 2019, the entire contents of which are hereby incorporated by reference.

FIELD

The present disclosure generally relates to devices, kits, and methods for encapsulating cells within a hydrogel. In particular, the present disclosure provides devices and methods for transplanting islet cells using a hydrogel macroencapsulation device prepared from an injection mold device.

BACKGROUND

Clinical islet transplantation is a promising treatment for insulin-dependent diabetic patients, with the potential to eliminate long-term secondary complications by restoring native insulin signaling. While clinical successes have demonstrated the feasibility of achieving insulin independence through islet replacement therapy, the necessity of a long term immunosuppressive regimen limits the widespread applicability of this procedure, as the substantial risk associated with chronic immunosuppression outweighs the risk of diabetes associated morbidities. For example, short-term graft lives may be caused by poor graft vascularization, a hostile graft microenvironment, ineffective and toxic immunosuppressive drug regimens, and immune rejection. The potent immune response to islets remains the greatest challenge to long-term engraftment and function, which necessitates large numbers of islets, and typically multiple pancreatic donors to achieve euglycemia, a complication further exacerbated by donor shortages.

As a result, research has explored the development of devices to isolate transplanted cells from the recipient immune system. Islet encapsulation within a biomaterial has been proposed as a means for reducing immune response to transplanted grafts via a physical barrier to direct antigen recognition by immune cells. Traditional techniques have used hydrogel microcapsules, on the scale of 600-1000 μm diameter, with limited translational success due to safety limitations of non-retrievable capsules within the intraperitoneal space. Human trials demonstrate microcapsule adhesion to parietal peritoneum, spleen, kidney, and omentum, raising concerns about the long-term safety of intraperitoneal capsule delivery. Device designs with the greatest potential for translation to the clinic include macroencapsulation devices, cell encapsulation devices which prioritize whole graft containment, retrievability, and safety. To date, these devices have demonstrated limited pre-clinical and clinical efficacy, due in large part to device transport issues: the diffusion of sufficient oxygen within the device to support encapsulated cell survival, as well as efficient insulin transport out of the device. Therefore, there is a critical need to rationally design macroencapsulation devices with optimal geometry that minimizes diffusion distances in order to maximize graft survival and function.

Vasculogenic degradable hydrogels have been shown to enhance vascularization, and therefore oxygenation, at the surface of macroencapsulation devices. However, despite improved vascularization, non-ideal device geometry limits encapsulated cell viability and function in vivo, as indicated by in silico modeling of device oxygenation.

Many macroencapsulation device designs require specialized assembly, equipment, or device fabrication, and this is particularly the case for fabricating hydrogel devices of complex 3D geometries. This limits the dissemination of these technologies to locations with the appropriate equipment and expertise. The ideal and most translational islet macroencapsulation strategy would employ a fabrication method requiring no specialized expertise or equipment, which can be readily implemented by a minimally trained clinician. As such, an injection molding-based strategy has been engineered for hydrogel macroencapsulation device fabrication, which enables macroencapsulation of cells at the patient's bedside via an off-the-shelf kit.

It is with these observations in mind, among others, that various aspects of the present disclosure were conceived and developed.

SUMMARY

Principles and embodiments of the present disclosure relate generally to hydrogel macroencapsulation devices, injection mold devices, and kits and methods of use thereof.

Some aspects of the disclosure relate to a hydrogel macroencapsulation device comprising: a biocompatible hydrogel operable to be crosslinked within an injection mold; and a plurality of cells encapsulated within the hydrogel. The hydrogel macroencapsulation device is formed from the injection mold, and the hydrogel macroencapsulation device has a geometry such that the plurality of cells encapsulated in the hydrogel are within 100 μm to 3000 μm from the edge of the hydrogel.

The biocompatible hydrogel may crosslink within 1-60 minutes. In some aspects, the biocompatible hydrogel is multi-arm PEG functionalized with bioorthogonal reactive groups. The plurality of cells may include islets. In various aspects, the geometry of the hydrogel macroencapsulation device is a spiral, a wrinkled sheet, a planar sheet, branched, or vascular.

Additional aspects of the disclosure include an injection mold device for forming a hydrogel macroencapsulation device, comprising: a bottom portion comprising one or more channels; and a top portion comprising complementary one or more channels to the channels in the bottom portion. When the bottom portion and top portion are connected together, they form a three-dimensional geometry with a diameter of 100 μm to 3000 μm.

In some aspects, the three-dimensional geometry is a spiral, a wrinkled sheet, a planar sheet, branched, or vascular. The one or more channels may form an inlet on an outside surface of the injection mold device and the one or more channels may end in an air vent. The air vent extends from an end of the one or more channels to an opening on an outside surface of the injection mold device.

In an aspect, the injection mold device further includes a middle portion comprising one or more channels, where the middle portion is operable to connect between the top portion and the bottom portion.

In various aspects, the bottom portion and the top portion are connected together by magnets or a clamp. The top portion may include one or more recessions on a top outer surface and the bottom portion each comprises one or more recessions on a bottom outer surface, and where in the clamp comprises two arms, each comprising one or more projections operable to connect to the one or more recessions on the top portion and the bottom portion.

Further aspects of the disclosure include a kit for forming a hydrogel macroencapsulation device comprising: the injection mold device; and a biocompatible hydrogel operable to be crosslinked within the injection mold.

In some aspects, the kit further includes a plurality of cells encapsulated within the hydrogel. For example, the plurality of cells may include islets. The biocompatible hydrogel may be multi-arm PEG functionalized with bioorthogonal reactive groups and the hydrogel macroencapsulation device may be formed from the injection mold. The hydrogel macroencapsulation device has a geometry such that the plurality of cells encapsulated in the hydrogel are within 100 µm to 3000 µm from the edge of the hydrogel.

Other aspects of the disclosure include a method of transplanting cells into a patient in need thereof, the method comprising: mixing a biocompatible hydrogel with a plurality of cells; injecting the mixture into an injection mold device with a three-dimensional geometry having a diameter of 100 µm to 3000 µm; crosslinking the hydrogel to form a hydrogel macroencapsulation device; removing the injection mold device after the hydrogel has crosslinked; and implanting the hydrogel macroencapsulation device into the patient.

BRIEF DESCRIPTION OF THE DRAWINGS

FIG. 2A shows rectangular sheet hydrogel macroencapsulation device oxygen gradients. Finite element modeling at varied oxygen consumption rates demonstrate oxygen gradients visually for cross sections of the device.

FIG. 2B shows oxygen concentration versus distance for different cell densities using the device of FIG. 2A.

FIG. 3A shows cylindrical sheet hydrogel macroencapsulation device oxygen gradients. Finite element modeling at varied oxygen consumption rates demonstrate oxygen gradients visually for cross sections of the device.

FIG. 3B shows oxygen concentration versus distance for different cell densities using the device of FIG. 3A.

Corresponding reference characters indicate corresponding elements among the view of the drawings. The headings used in the figures do not limit the scope of the claims.

DETAILED DESCRIPTION

Figure 1A:
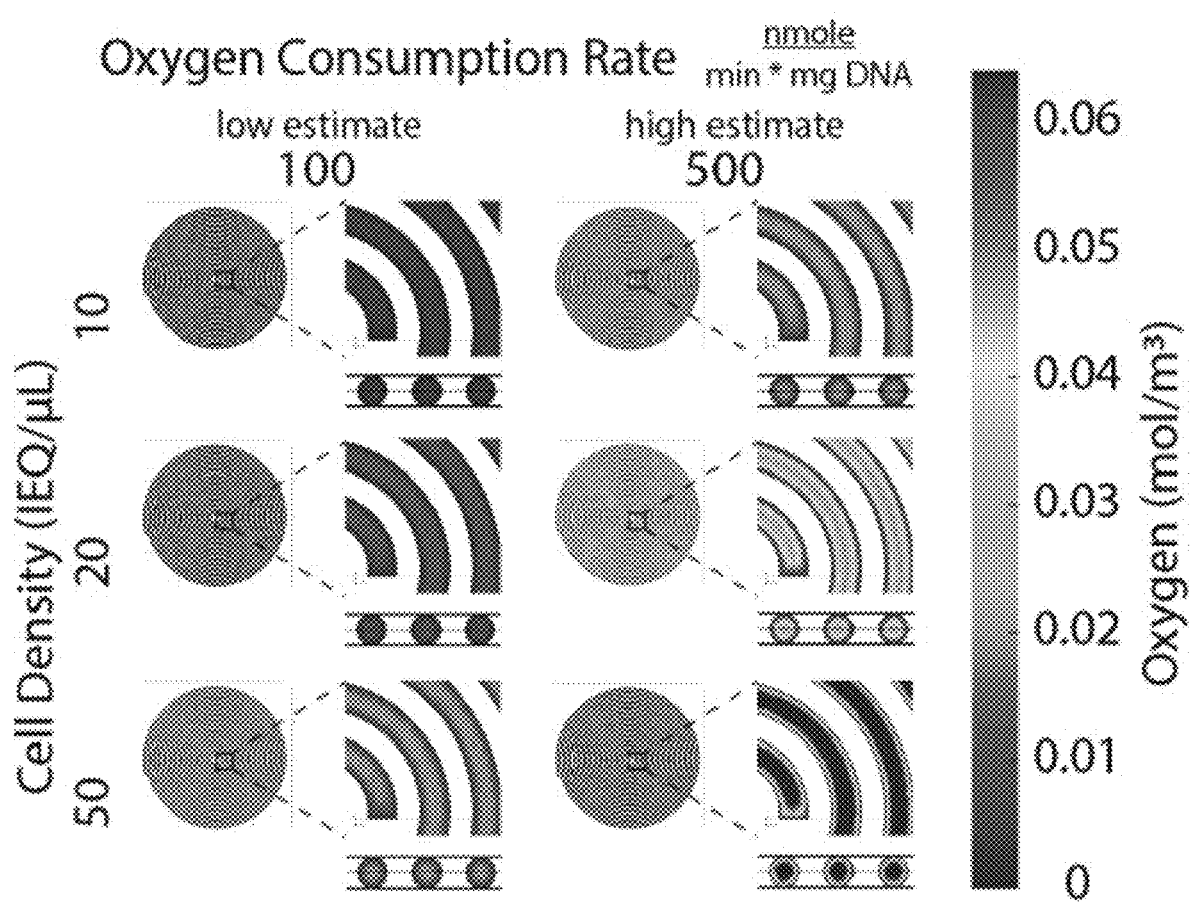
FIG. 1A shows spiral hydrogel macroencapsulation device oxygen gradients. Finite element modeling at varied oxygen consumption rates demonstrate oxygen gradients visually for cross sections of the device.

The present disclosure provides devices and kits for encapsulating cells within a hydrogel. The present disclosure also provides methods for transplanting islet cells using a hydrogel macroencapsulation device. An advantage of the devices and methods disclosed herein is that they allow for the formation of complex geometries to provide optimal oxygenation to the cells. Another advantage is bedside implementation of cell encapsulation. Other aspects of the device and methods of the present disclosure are described more thoroughly below.

Several definitions that apply throughout this disclosure will now be presented. As used herein, "about" refers to numeric values, including whole numbers, fractions, percentages, etc., whether or not explicitly indicated. The term "about" generally refers to a range of numerical values, for instance, ±0.5-1%, ±1-5% or ±5-10% of the recited value, that one would consider equivalent to the recited value, for example, having the same function or result.

The term "comprising" means "including, but not necessarily limited to"; it specifically indicates open-ended inclusion or membership in a so-described combination, group, series and the like. The terms "comprising" and "including" as used herein are inclusive and/or open-ended and do not exclude additional, unrecited elements or method processes. The term "consisting essentially of" is more limiting than "comprising" but not as restrictive as "consisting of." Specifically, the term "consisting essentially of" limits membership to the specified materials or steps and those that do not materially affect the essential characteristics of the claimed invention.

As islets exhibit oxygen consumption rates up to 1000-fold higher than other cell types, the primary limitation of macroencapsulation devices is adequate oxygenation of encapsulated islets due to isolation from high oxygen vascular tissue in order to prevent immune recognition. As such, it is critical that islet macroencapsulation devices are designed for optimal geometry with respect to oxygen distribution, prioritizing device designs which minimize distance between islet and vascular tissue, thereby maximizing device oxygenation. Spatial oxygen gradients within cell macroencapsulation devices represent a critical barrier to the translation of islet replacement therapy in the absence of an immunosuppressive drug regimen.

Macroencapsulation device designs which limit diffusion distances also confer the benefit of minimal excess material, resulting in high cell density devices that have greater potential to scale to larger animal models or humans. For example, microencapsulation with a typical capsule size of 1 mm diameter, with a maximal cell density of 3 islets per capsule, results in 140 mL of material and cell graft volume. This quantity of material limits transplantation to large sites such as the intraperitoneal cavity. By comparison, a spiral macroencapsulation device of the same 1 mm diameter but 254 cm length results in maximal volume of 2 mL at a comparable cell density. The geometry improves oxygen gradients, and the 10-fold reduction in volume results in greater flexibility in transplantation site, potentially enabling transplantation in highly vascularized tissue such as the omentum. Proximity to highly vascularized tissue maximizes oxygen tension at the surface, and therefore maximizes device internal oxygenation. Additionally, typical microencapsulation techniques require specialized equipment by a trained user, which reduces the wide-spread use of this technique. Alternatively, an injection-molding strategy may enable fabrication of complex device geometries, and facilitate facile implementation in the clinic, as this technique minimizes specialized equipment or training required for device fabrication.

Provided herein are a multi-component injection mold device, a hydrogel macroencapsulation device, and a kit including the injection mold device and the hydrogel for creating the hydrogel macroencapsulation device with embedded cells. The hydrogel macroencapsulation device created using the injection mold device may have a three-dimensional (3D), complex geometry that provides adequate oxygenation to the embedded cells after implantation in the body. The hydrogel macroencapsulation device may utilize hydrogel reaction schemes specific for use with the injection mold to allow the hydrogel to be fully injected into the injection mold before the hydrogel crosslinks.

I. Hydrogel Macroencapsulation Device

Provided herein is a hydrogel macroencapsulation device to house and support cells for transplantation and physically isolate the cells from the recipient immune system. The macroencapsulation device may house and support cells for transplantation, and shield them from direct antigen recognition by the recipient immune system. A primary limitation of previous macroencapsulation device iterations is their oxygen transport properties, which limit survival of transplanted cells. The hydrogel macroencapsulation device may have any geometry that reduces oxygen diffusion distances within the device sufficiently to preserve and maintain cell viability and function. For example, geometric device designs may be selected based on performance in finite element modeling of device oxygen profile. In some examples, the hydrogel macrencapsulation device may have a spiral shape, as seen in FIG. 1A, FIGS. 4D-4E, and FIGS. 5H-5K, channels in a planar sheet, as seen in FIG. 2A, channels in a crimped sheet, channels in a cylindrical sheet, as seen in FIG. 3A, or channels in a branched arrangement or vascular arrangement. FIGS. 1A-3B show example hydrogel macroencapsulation device geometries with finite element modeling to demonstrate oxygen gradients within devices of varied geometries. As seen in FIGS. 4B-4C, 5B-5C, 6B-6C, 7A-7B, 8B-8D, 9B-9C, 10B-10C, and 11B-11C, the geometry of the hydrogel macroencapsulation device may be formed by a channel in an injection mold device shaped into the geometry such that the diffusion distance through the hydrogel is minimized.

In some examples, cells within the hydrogel may be within about 100 μm to about 3000 μm from the edge of the hydrogel, providing sufficient oxygenation to the cells encapsulated within the device. In various examples, the cells within the hydrogel may be within about 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm from the edge of the hydrogel, or any range between these values.

In some examples, the channel or channels forming the complex geometry of the hydrogel macroencapsulation device may have a diameter of about 100 μm to about 3000 μm. In various examples, the channel or channels forming the complex geometry of the hydrogel macroencapsulation device may have a diameter of about 100 μm, 150 μm, 200 μm, 250 μm, 300 μm, 350 μm, 400 μm, 450 μm, 500 μm, 550 μm, 600 μm, 650 μm, 700 μm, 750 μm, 800 μm, 850 μm, 900 μm, 950 μm, 1000 μm, 1500 μm, 2000 μm, 2500 μm, 3000 μm, or any range between these values.

The hydrogel macroencapsulation device may have a size of up to about 10 cm by 10 cm. In some embodiments, the hydrogel macroencapsulation device may have a size of up to about 8.3 cm by 8.3 cm. In at least one example, the hydrogel macroencapsulation device may have a size of up to about 6 cm by 6 cm. In some examples, the height of the hydrogel macroencapsulation device may range from about 1 μm to about 3 cm. In at least one example, the hydrogel macroencapsulation device may have a height of about 1 mm. The hydrogel macroencapsulation device may be sized for implantation in a human.

The hydrogel macroencapsulation device includes a hydrogel polymer and a plurality of cells to be encapsulated within the hydrogel. The plurality of cells may include any cell to be transplanted within a patient's body. In at least one example, the cells to be encapsulated and/or transplanted includes islets. In some examples, the hydrogel may encapsulate a range of cell densities between about 1 islet equivalent (IEQ)/μL and about 50 IEQ/μL. The cell density in the hydrogel may be about 1 IEQ/μL, up to about 10 IEQ/μL, up to about 20 IEQ/μL, up to about 30 IEQ/μL, up to about 40 IEQ/μL, up to about 50 IEQ/μL, or any range between these values. In some examples, the hydrogel macroencapsulation device may include a maximum of 100,000 IEQ cells per device to limit loss of cell viability and function. The typical yield of islets from a human pancreas ranges from 200,000-600,000 IEQ. As such, a single islet transplantation may require between 2-6 hydrogel macroencapsulation devices. In some examples, the multiple hydrogel macroencapsulation devices may be stacked. The macroencapsulation devices may be stacked directly on top of each other. The macroencapsulation devices may be stacked in a variety of orientations. The macroencapsulation devices may be stacked vertically with or without rotation, with or without translation, with or without reflection, or with or without resizing of each subsequent layer. In some examples, the multiple hydrogel macroencapsulation devices may be placed side by side. In other examples, the macroencapsulation devices may be placed side by side and stacked, in any combination.

In some examples, the hydrogel macroencapsulation device may protect encapsulated allogeneic cells from physical contact with the host immune response, maximize cell viability and function through optimization of geometry and encapsulating material, and which prioritizes facile device implementation in the clinic and automation and scale-up by fabrication via injection molding. In an example, the hydrogel macroencapsulation device may be designed for delivery to defined transplant sites, and for retrievability to maximize device safety. An example application is islet transplantation, where allogeneic insulin producing cells are protected from immune attack by the hydrogel encapsulation material. The hydrogel macroencapsulation device may have a complex geometry, created by using an injection mold device with the complex geometry.

The hydrogel may be suitable for use in the injection molding scheme. The hydrogel may have a highly controlled and tunable matrix design and crosslinking. In some examples, to generate hydrogels within injection molds, a cell-compatible hydrogel crosslinking scheme is needed with reaction kinetics in the range of 1-60 minutes, and good in vivo stability. In various examples, the biocompatible hydrogel may crosslink within 1 minute, 5 minutes, 10 minutes, 15 minutes, 20 minutes, 25 minutes, 30 minutes, 40 minutes, 50 minutes, or 60 minutes. Biocompatible synthetic or natural hydrogels may be used to form the hydrogel macroencapsulation device. Non-limiting examples of hydrogels for forming the hydrogel macroencapsulation device include poly(ethylene glycol) (PEG), agarose, and alginate. In at least one example, PEG may be used due to their tenability and reproducibility in manufacturing and scaling. Typical synthetic hydrogel matrices are designed for in situ use, necessitating fast-polymerizing polymers. However, hydrogels with slower polymerization rates may be beneficial in an injection molding scheme, where sufficient time is required to mix components and inject into the mold. Advantages over faster-crosslinking hydrogels include greater uniformity and homogeneity in final hydrogel product crosslinking, expected to result in greater consistency of performance in vivo. In some examples, the macroencapsulation device may utilize a PEG biorthogonal reaction scheme, which has high biocompatibility and crosslinks under conditions such that it may be used with the injection mold.

Table 1 provides a library of compatible hydrogel reaction schemes that may be deployed within the injection mold. In some examples, hydrogel components may include (1) multi-arm PEG macromer, in the range of 10-50 kDa, functionalized with bioorthogonal reactive groups (Table 1), (2) bioactive molecules, peptides and proteins to support cell function and viability, including any bioactive factors that can be bound to the matrix, and (3) crosslinker(s) with reactive groups corresponding to the bioorthogonal reacted groups listed in Table 1, with either a nondegradable spacer (PEG 0.5-10 kDa), or a proteolytically degradable peptide. Non-limiting examples of bioactive molecules, peptides, and proteins include peptide adhesive ligands (e.g. RGD, GFOGER, IKVAV), bioactive molecules (e.g. VEGF, PDGF-BB, and other signaling proteins), and immunomodulatory agents (e.g. HLA-G, galectin-1, galectin-3, etc.).

TABLE 1

| Reactive group | | Abbreviation |
|---|---|---|
| Bio-orthogonal reactive group | | |
| tetrazine | norbonene | NB |
| | (E)-cyclooct-4-enol | TCO |
| azide | dibenzocyclooctyne | DBCO |
| | azidodibenzocyclooctyne | ADIBO |
| | dibenzoazacyclooctyne | DIBAC |
| | difluorocyclooctyne 2 | DIFO2 |
| | difluorocyclooctyne 3 | DIFO2 |
| | bicyclononyne | BCN |
| thiol | maleimide | MAL |
| | iodoacetamide | IODO |
| Polymer backbone | | |
| | 4-arm poly(ethylene glycol), 10-80 kDa | |
| | Alginate | |
| | Agarose | |

In some examples, the hydrogel may include a vasculogenic hydrogel to encourage vascularization at the macroencapsulation device surface. Maximal oxygenation within the hydrogel macroencapsulation device is dependent upon the oxygen levels of tissue at the surface of the device. The higher the density of oxygen-rich vascular networks at the surface of the device, the higher the oxygenation within the device. Therefore, the optimal configuration of this invention would include a coating of vasculogenic degradable hydrogel at the device surface upon implantation.

II. Injection Mold Device

Provided herein is a multi-component injection mold device to fabricate hydrogel macroencapsulation devices of complex geometries. The complex geometries are needed for macroencapsulation to provide adequate oxygenation of encapsulated cells. However, because hydrogels need time to crosslink, forming complex geometries has previously been difficult without complex equipment and skilled implementation (e.g. 3D printing, light activated crosslinking). The injection mold device allows for the creation of complex hydrogel geometries without complex equipment or skilled implementation. In some examples, the injection mold device may provide a mold in which to form a hydrogel into a complex geometry, such as a spiral, blood vessel branches, a capillary bed, or any other three-dimensional geometry. Using an injection mold, the hydrogel may have sufficient time to crosslink prior to removal of the mold.

In some embodiments, the injection mold device is used to form a hydrogel macroencapsulation device. The injection mold generates hydrogels of complex 3D shapes in a clinically translatable manner. In some examples, the injection mold includes assembled mold parts and a custom clamp to secure the mold during hydrogel crosslinking. The injection mold may include a two-part design (top and bottom sections) or three-part design (top, middle, and bottom sections). In some examples, the sections of the injection mold may be held together with magnets or a clamp. In some examples, the injection mold and clamp may be fabricated via 3D printing. In other examples, commercially-made device components may be injection molded and mass produced. The injection mold may be scaled for automated and reproducible construct fabrication.

Example injection mold device designs are exhibited in FIGS. 4A-11F. FIGS. 4A-7B and 9A-11C show a two-part mold and FIGS. 8A-8D show a three-part mold designed for use with a custom-designed clamp (FIGS. 12A-12B and 13A-13B). FIGS. 4A-8D and 11A-11C show examples of various embodiments of the injection mold device for generating a spiral hydrogel macroencapsulation device. FIGS. 9A-10C show examples of vascular embodiments of the injection mold device for generating a biomimetic or vascular shaped hydrogel macroencapsulation device. FIGS. 7A-7B show examples of a mold for multiple hydrogel macroencapsulation devices. In this example, a single mold may create more than one hydrogel at the same time.

In some embodiments, as seen in FIGS. 4A-11F, the injection mold device 100 may include a top portion 102 having one or more channels 106 and a bottom portion 104 having one or more channels 106. The one or more channels 106 in the top portion 102 and the bottom portion 104 are arranged in a desired configuration. In some examples, the bottom portion 104 may include a raised platform 116 where the channels 106 are located and the top portion 102 may include a chamber 118 where the channels 106 are located, where the chamber 118 is sized to receive the platform 116 of the bottom portion 104. The platform 116 may be inset such that it has a smaller perimeter than the perimeter of the bottom portion 104. Similarly, the chamber 118 may be inset such that it has a smaller perimeter than the perimeter of the top portion 102. The bottom portion 104 may include more than one platforms, each having one or more channels 106, as seen in FIGS. 7A and 7B.

In some embodiments, the injection mold device 100 may further include a middle portion 108 having one or more channels 106, where the middle portion 108 is operable to connect between a top portion 102 and a bottom portion 104, as seen in FIGS. 8A-8D. In this example, the top portion 102 and the bottom portion 104 may each include a platform 116 with the one or more channels 106, while the middle portion 108 includes two complementary chambers 118 for receiving the top portion 102 and the bottom portion 104, respectively. The use of a middle portion is intended to facilitate hydrogel device extraction from the injection mold. The top portion 102, the bottom portion 104, and/or the middle portion 108 are operable to connect together, such that the channels 106 of each portion are complementary and align to form a 3D conformation. The channels 106, and therefore the 3D conformation, may be a spiral, channels in a planar sheet, channels in a crimped sheet, channels in a cylindrical sheet, channels forming blood vessel branches, channels forming a capillary bed, or any other complex geometry.

Figure 15:
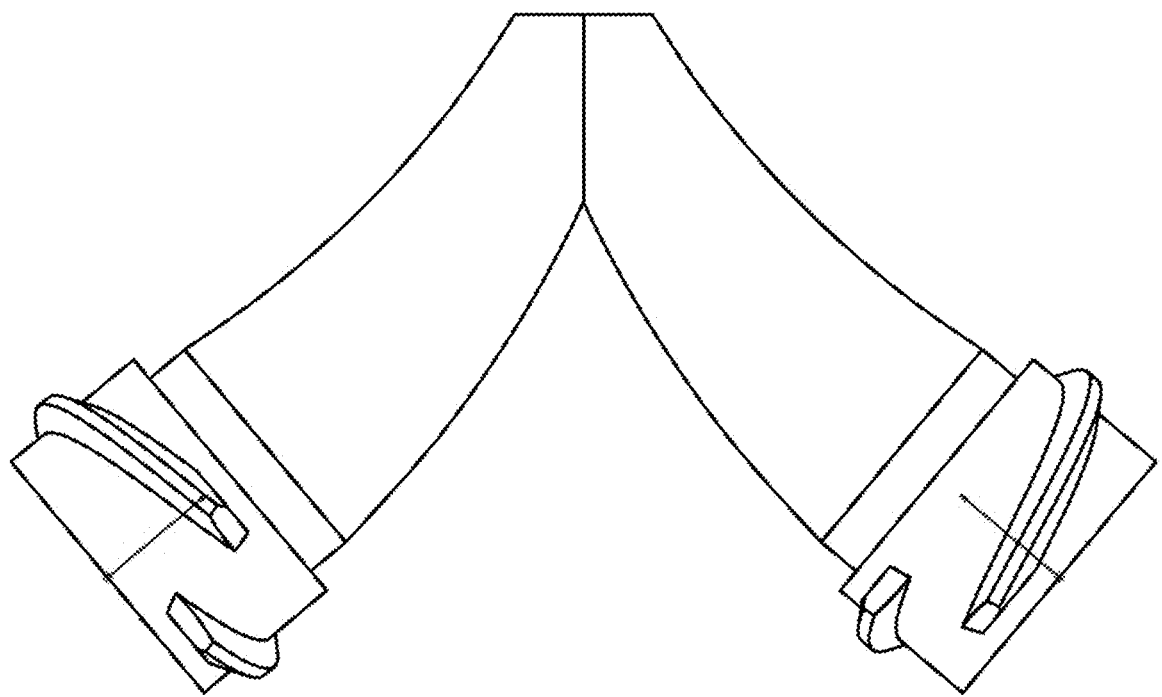
FIG. 15 is an example of a multicomponent injection port for use with multicomponent hydrogels in injection molds.
Figure 16:
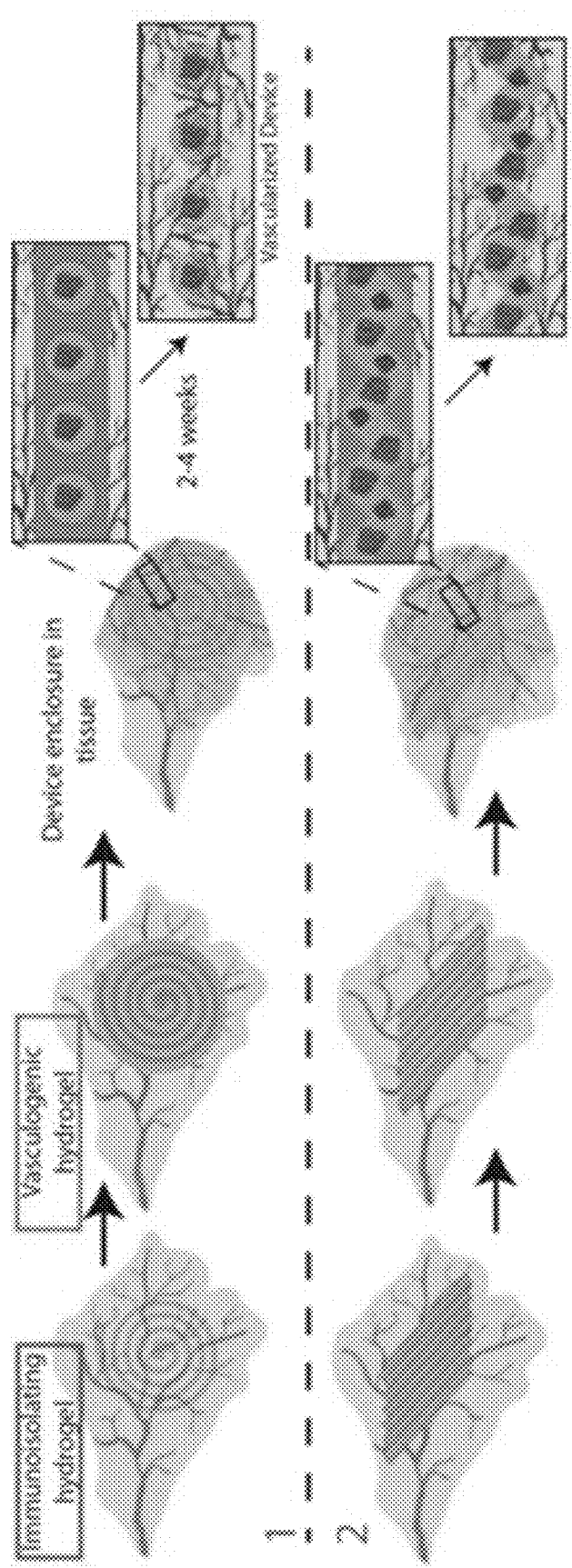
FIG. 16 shows example configurations of macroencapsulation devices which minimize diffusion distances between encapsulated cells and surrounding vasculature.

The one or more channels 106 in the top portion, bottom portion, and/or middle portion may form an inlet 112 in the side of the injection mold device 100 when the top portion 102, the bottom portion 104, and/or the middle portion 108 are connected together. The hydrogel with cells may be injected into the injection mold device 100 through the inlet 112. Cells are mixed with solubilized hydrogel components, provided per device, at an appropriate density. In some embodiments, the inlet may be operable to receive a multicomponent injection port for use with multicomponent hydrogels in injection molds, as seen in FIG. 15. The multicomponent injection port may allow for two components to be injected into the inlet simultaneously so that the two components can mix within the one or more channels. The one or more channels 106 may have one or more air vents 114. In an embodiment, the air vent 114 may be a channel that extend from the end of a channel 106 to an opening on the top or side of the injection mold device 100. The air vents 114 allow flow of the hydrogel through the channels. The air vents 114 may range in size depending on the flow needed for the design and the viscosity of the hydrogel being injected.

FIGS. 4F-4H, 5D-5F, 6D-6F, 9D-9F, 10D-10F, and 11D-11F show pressure, shear rate, and velocity flow trajectories through various channel conformations. The pressure, shear rate, and velocity of the hydrogel with encapsulated cells should be fast and strong enough for the hydrogel to flow through the entire length of the channel, while minimizing forces that could damage the cells.

Figure 14:
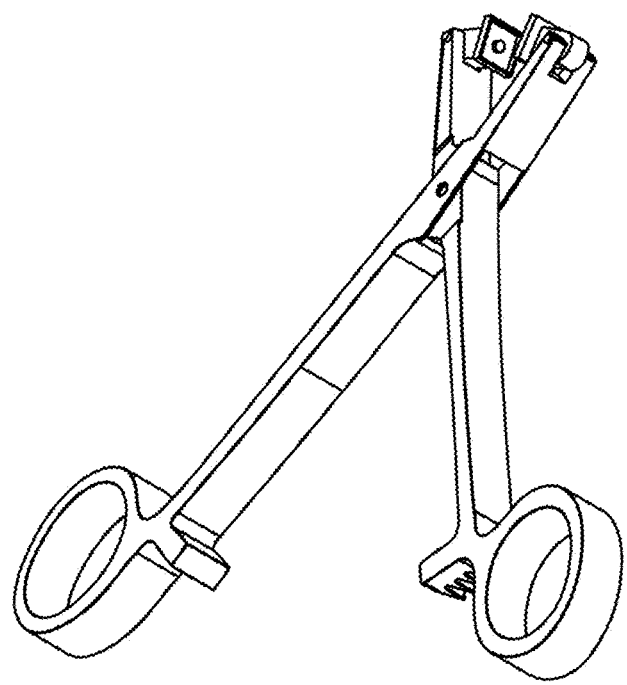
FIG. 14 is an example of a hemostat clamp.

The top portion 102, the bottom portion 104, and/or the middle portion 108 may be connected together using magnets to generate a seal between the mold components. In some examples, the top portion 102, the bottom portion 104, and/or middle portion 108 may be press fit together. In various embodiments, the top portion 102, the bottom portion 104, and/or the middle portion 108 may be held together using a clamp 200. The clamps are operable to create a sufficient seal on the injection mold device so there is not leakage of the hydrogel when injecting it. The clamp 200 may include two clamp arms 202 operable to clamp the top portion, the bottom portion, and/or the middle portion together. In some embodiments, the top portion 102 and/or the bottom portion 104 may include one or more recessions 110 on an outer surface (see FIG. 11A). In an example, the top portion 102 comprises one or more recessions 110 on a top outer surface and the bottom portion 104 each comprises one or more recessions 110 on a bottom outer surface. The one or more recessions 110 may be operable to engage with one or more protrusions 204 on the two clamp arms 202, as seen in FIGS. 12A-12B and 13A-13B. FIG. 14 is an example hemostat injection mold clamp. In some examples, the hemostat injection mold clamp may be easily used in the surgical suite by surgeons because it has a familiar shape and feel to other tools that surgeons are familiar with and surgeons may feel more comfortable using the hemostat injection mold clamp in the clinic.

The top portion 102, middle portion 108, and or bottom portion 104 of the injection mold device may have a square or rectangular cross section. For example, the injection mold device may have a square cross section, as seen in FIGS. 4A-6C and 8A-8C, or a rectangular cross section, as seen in FIGS. 7A-7C and 9A-11C. In some examples of a rectangular injection mold device, the bottom portion 104 (and corresponding top portion 102) may include more than one separate channels operable to form more than one hydrogel macroencapsulation devices simultaneously. In one example, referring to FIGS. 7A-7C, the top portion 102 and the bottom portion 104 may include eight spiral channels 106 operable to form eight hydrogel macroencapsulation devices.

Figure 6A:
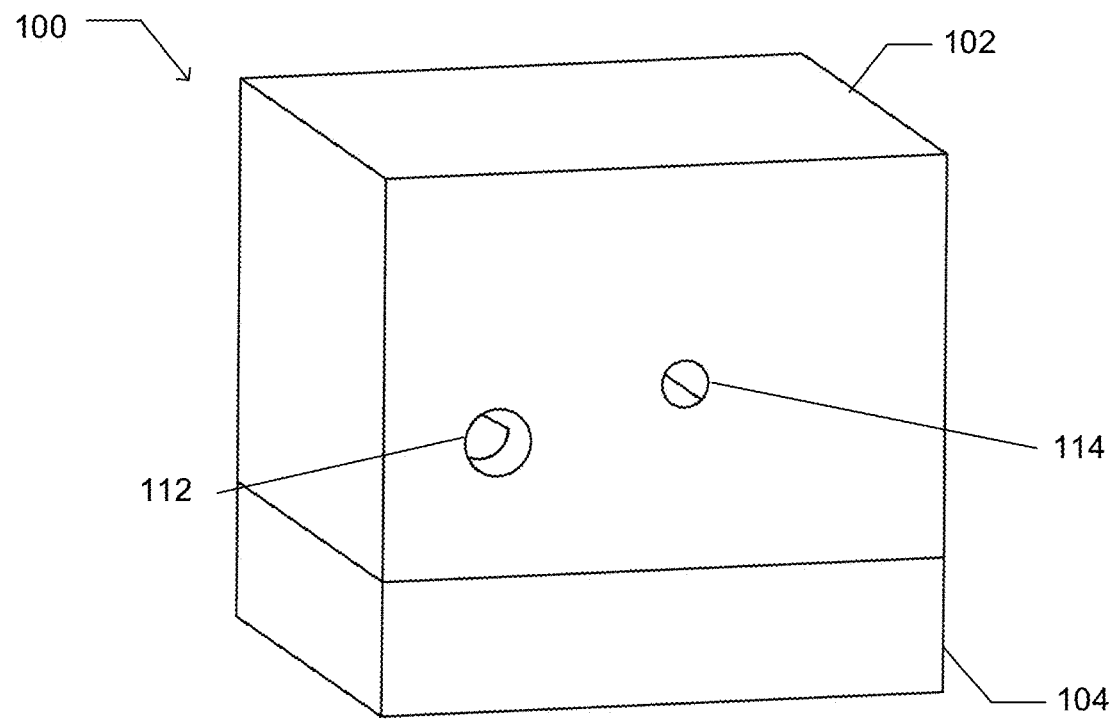
FIG. 6A is an example assembly for a 0.5 mm diameter spiral embodiment of the injection mold.
Figure 6B:
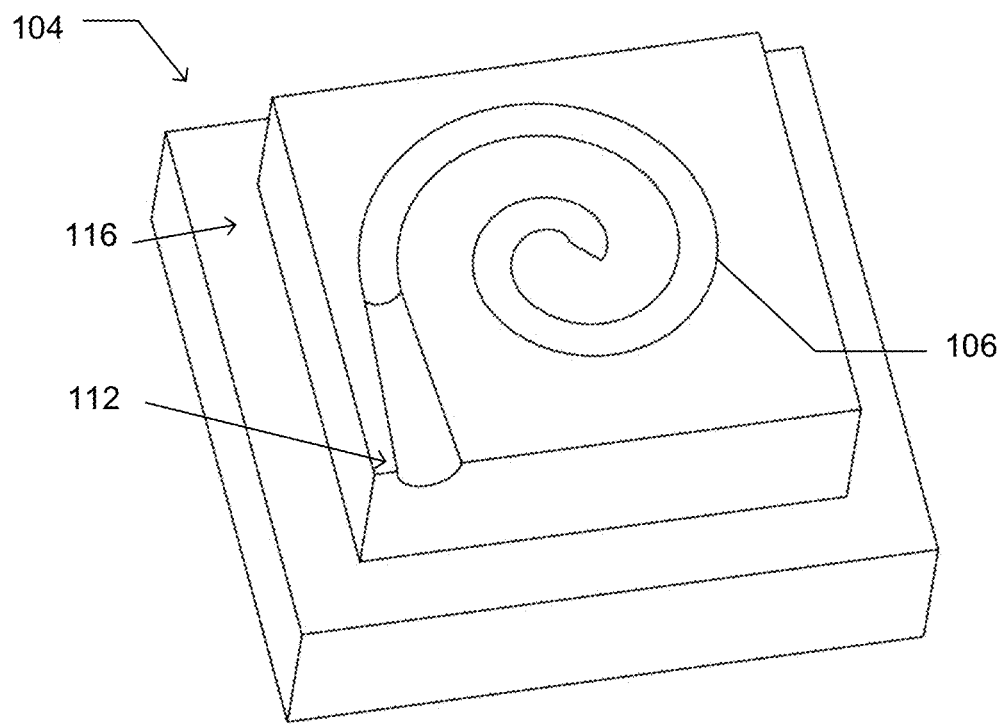
FIG. 6B is an example bottom portion of an assembly for a 0.5 mm diameter spiral embodiment of the injection mold.
Figure 6C:
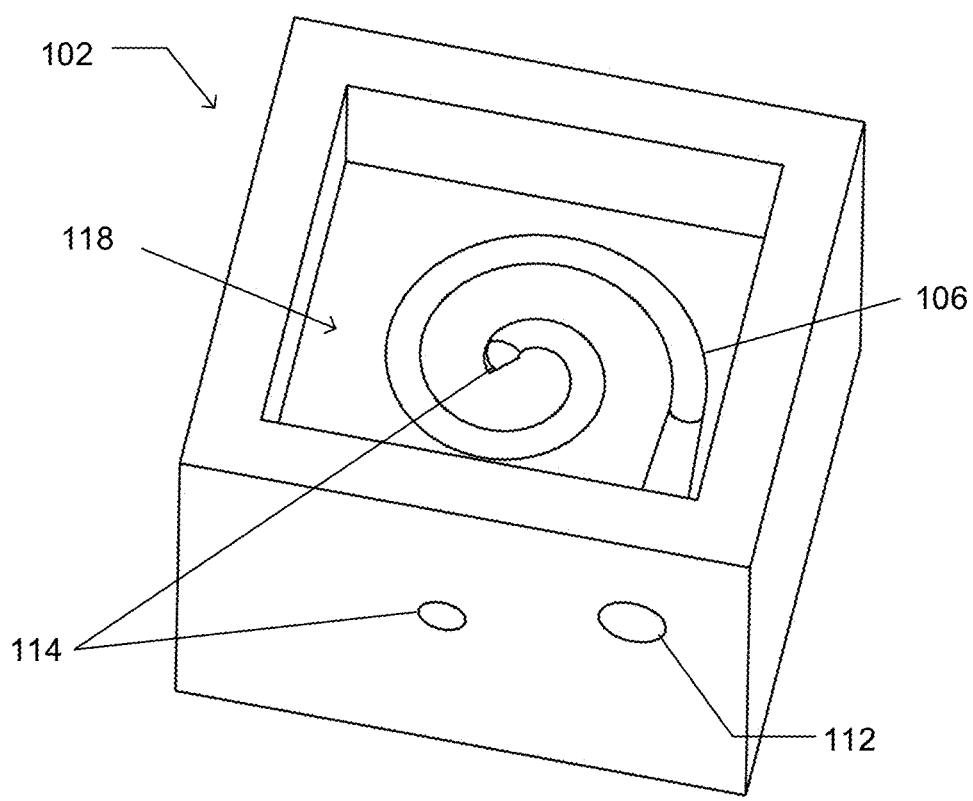
FIG. 6C is an example top portion of an assembly for a 0.5 mm diameter spiral embodiment of the injection mold.
Figure 6D:
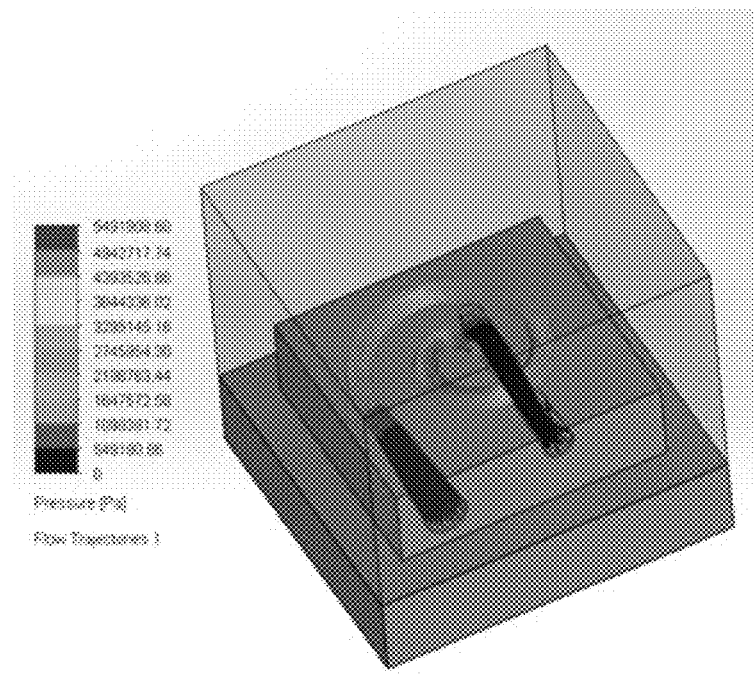
FIG. 6D is a fluid flow simulation for pressure in a 0.5 mm diameter spiral embodiment of the injection mold.
Figure 6E:
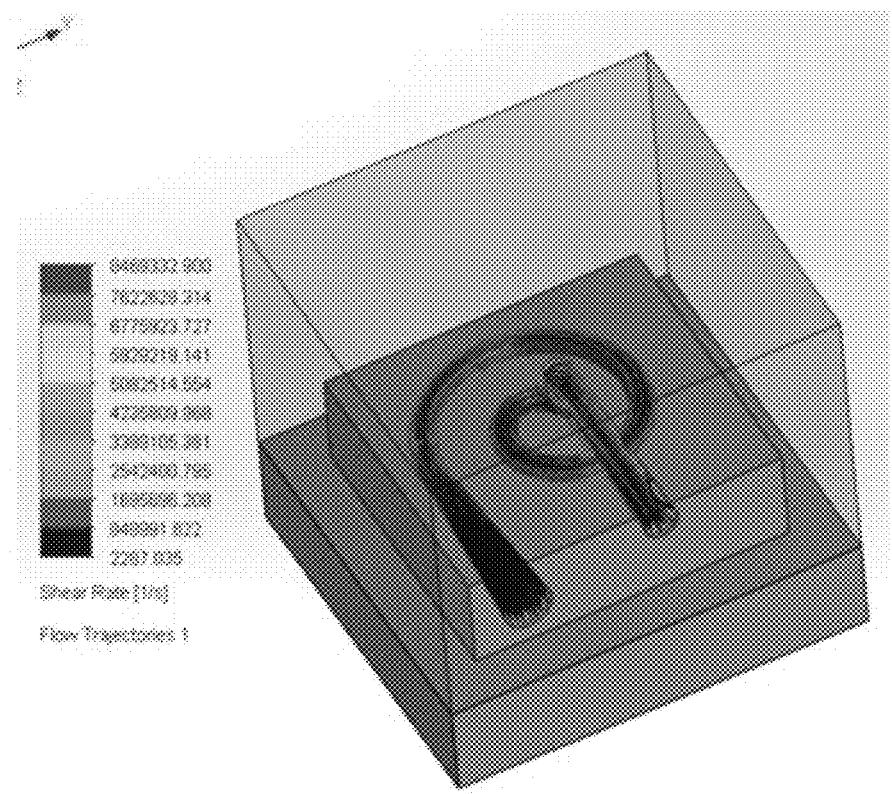
FIG. 6E is a fluid flow simulation for shear rate in a 0.5 mm diameter spiral embodiment of the injection mold.
Figure 6F:
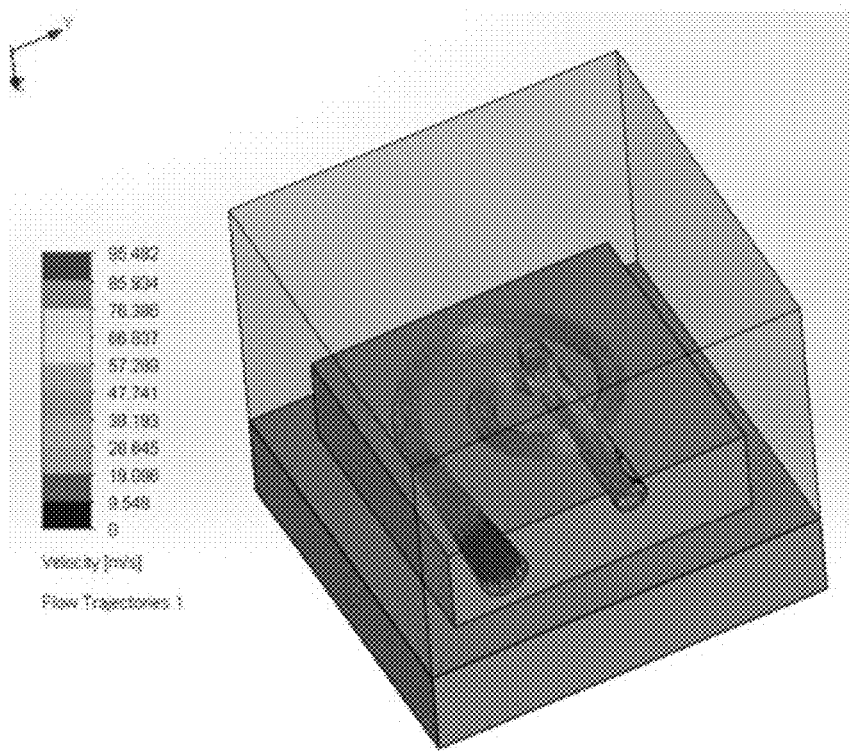
FIG. 6F is a fluid flow simulation for velocity in a 0.5 mm diameter spiral embodiment of the injection mold.
Figure 7A:
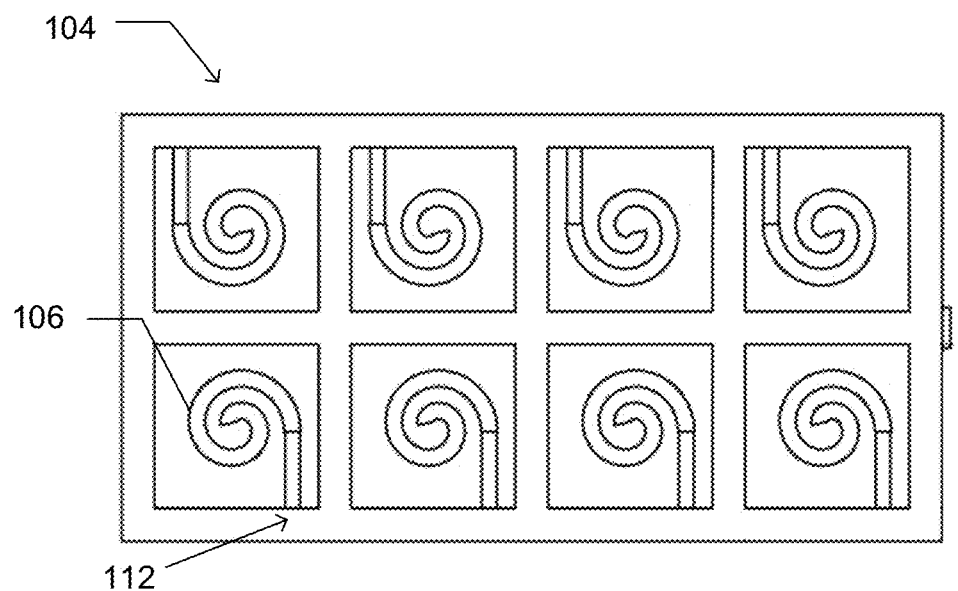
FIG. 7A is an example bottom portion of an assembly for a multi spiral embodiment of the injection mold.
Figure 7B:
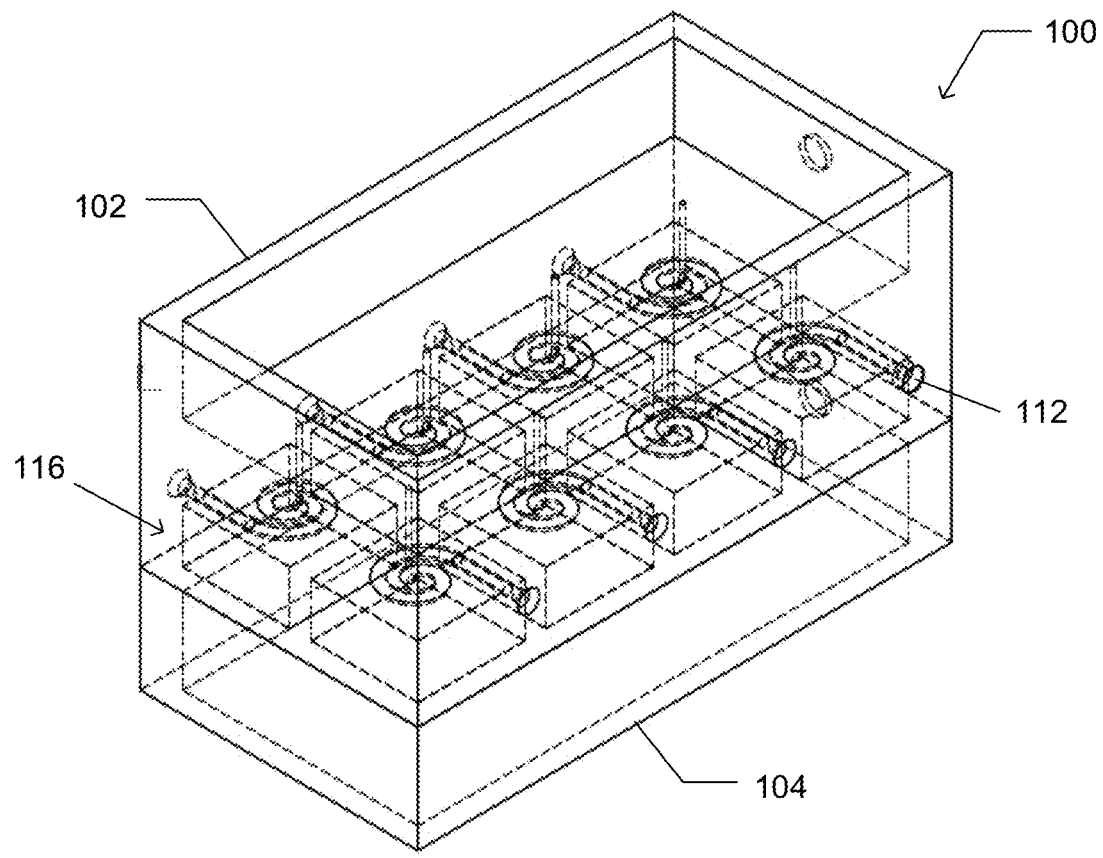
FIG. 7B is an example assembly for a multi spiral embodiment of the injection mold.
Figure 8A:
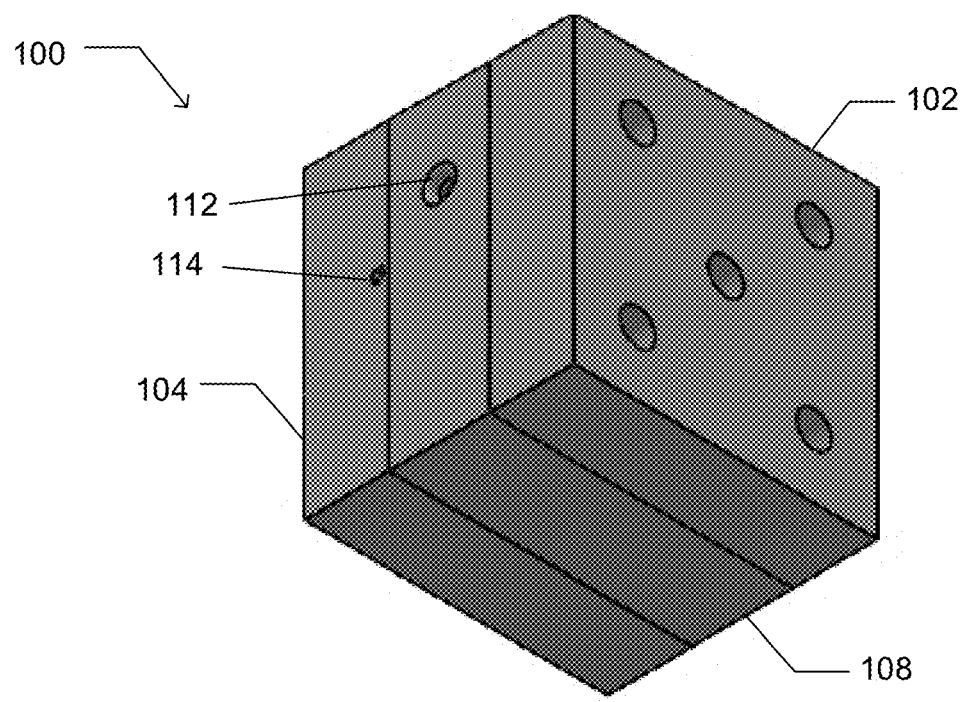
FIG. 8A is an example assembly for a three component embodiment of the injection mold.
Figure 8B:
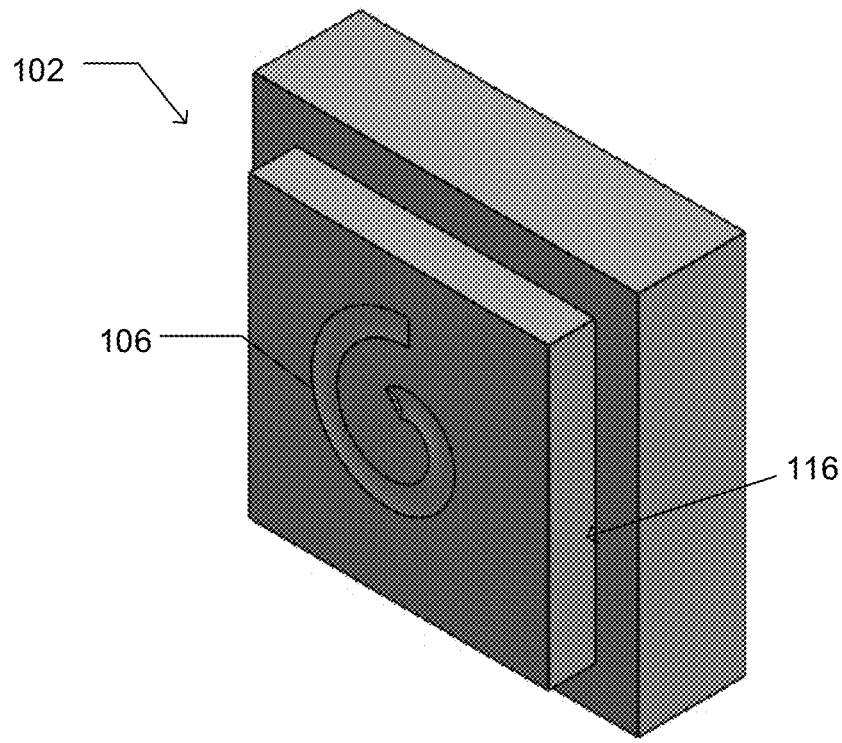
FIG. 8B is an example top portion of a three component embodiment of the injection mold.
Figure 8C:
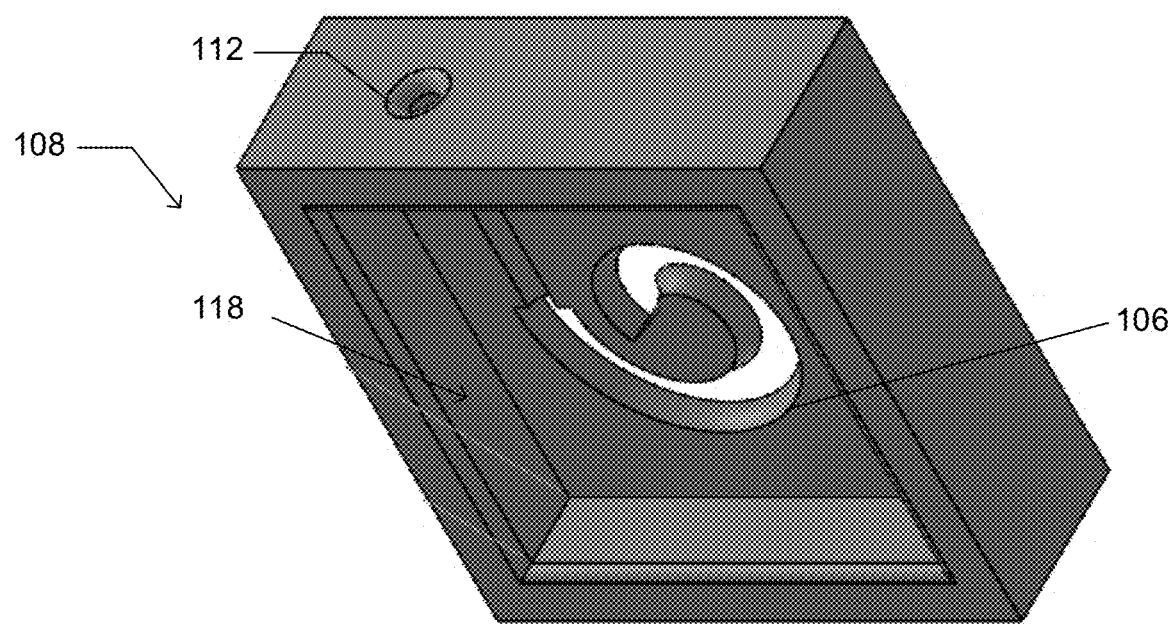
FIG. 8C is an example middle portion of a three component embodiment of the injection mold.
Figure 8D:
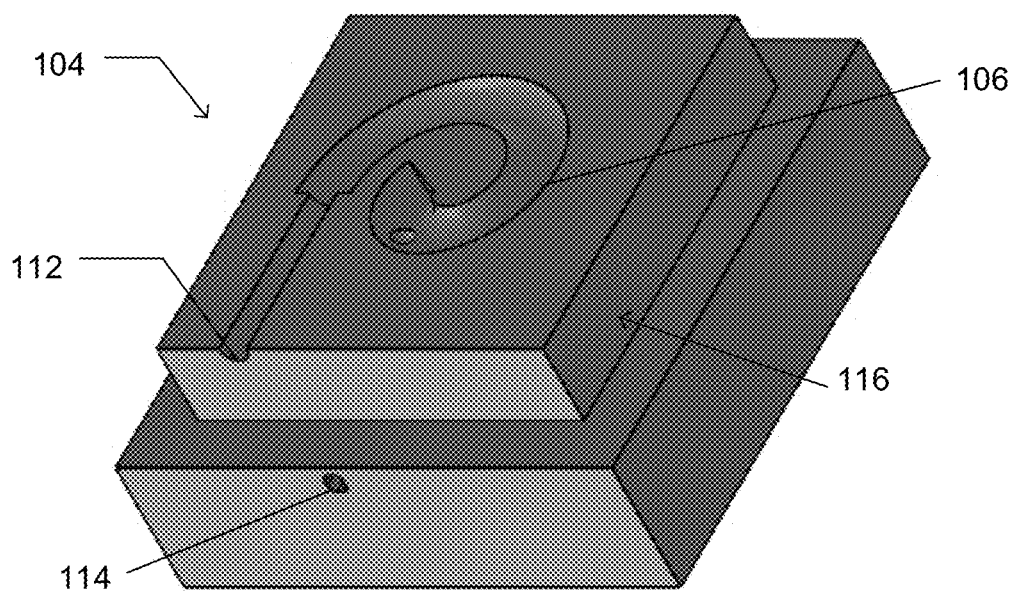
FIG. 8D is an example bottom portion of a three component embodiment of the injection mold.
Figure 9A:
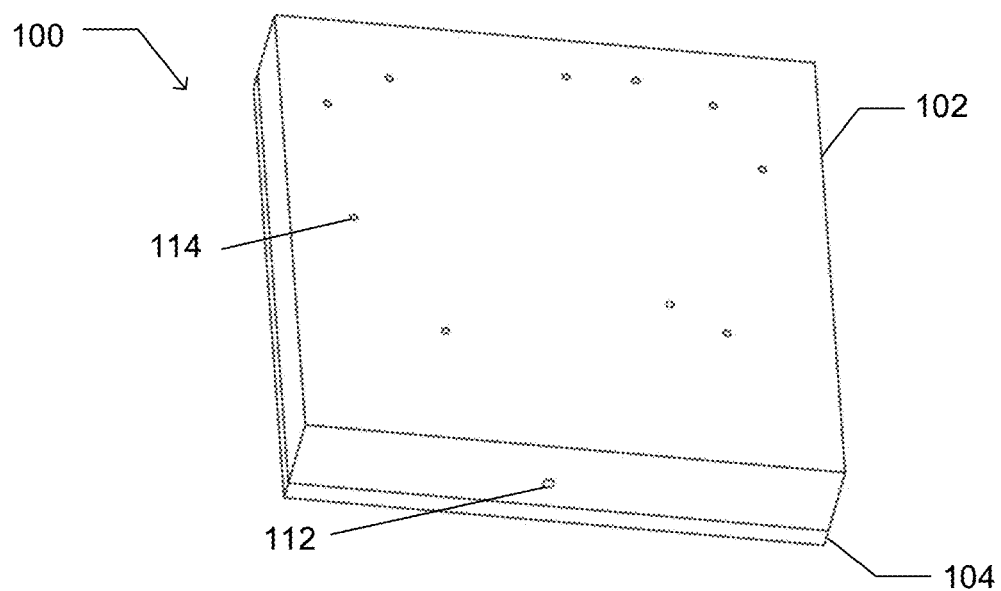
FIG. 9A is an example injection mold assembly for blood vessel branches.
Figure 9B:
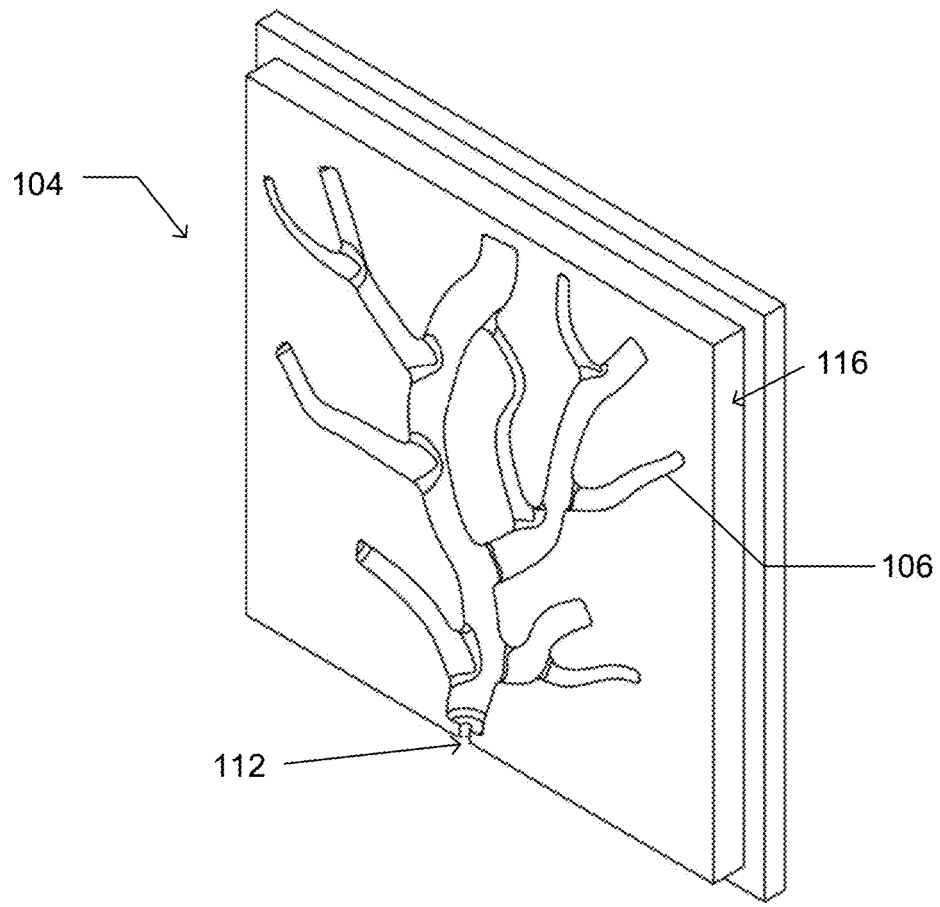
FIG. 9B is an example bottom portion of an injection mold assembly for blood vessel branches.
Figure 9C:
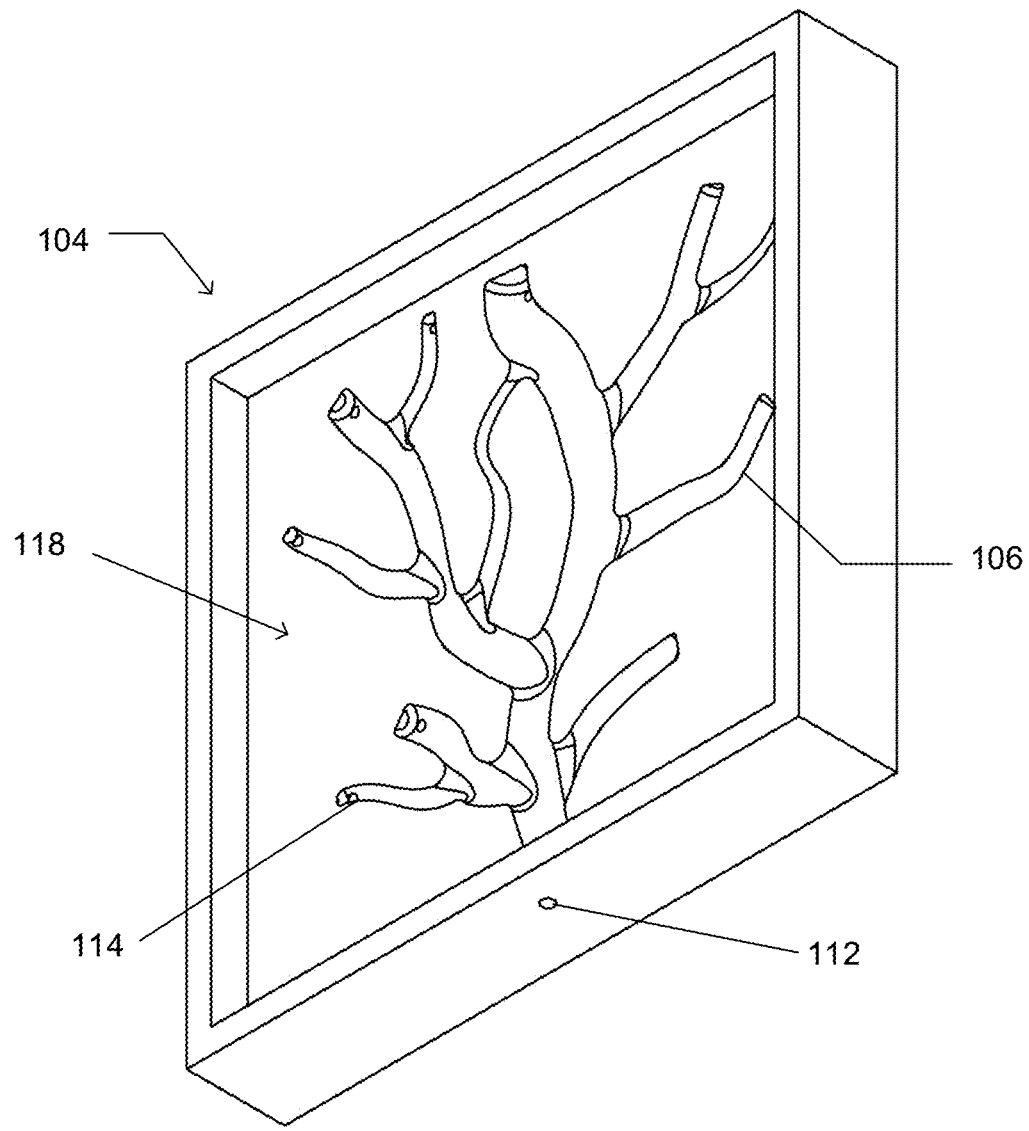
FIG. 9C is an example top portion of an example injection mold assembly for blood vessel branches.
Figure 9D:
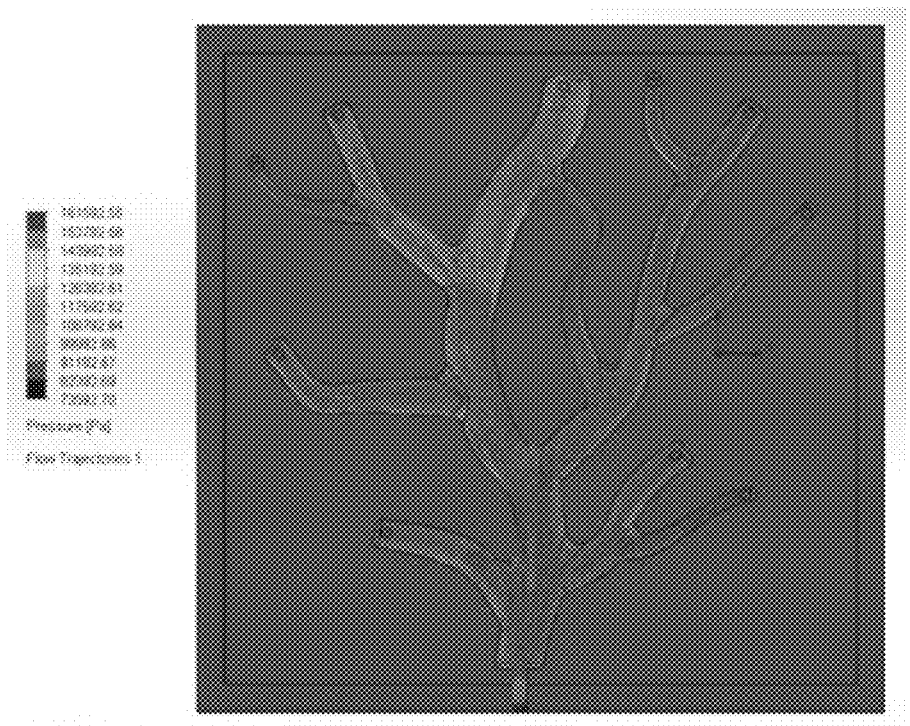
FIG. 9D is a fluid flow simulation for pressure in blood vessel branches.
Figure 9E:
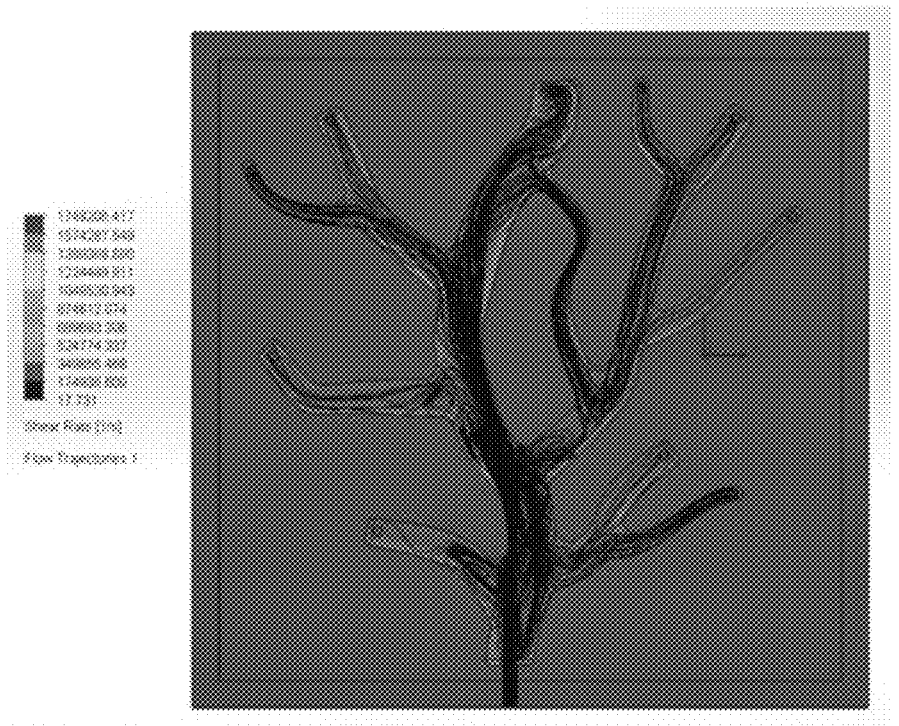
FIG. 9E is a fluid flow simulation for shear rate in blood vessel branches.
Figure 9F:
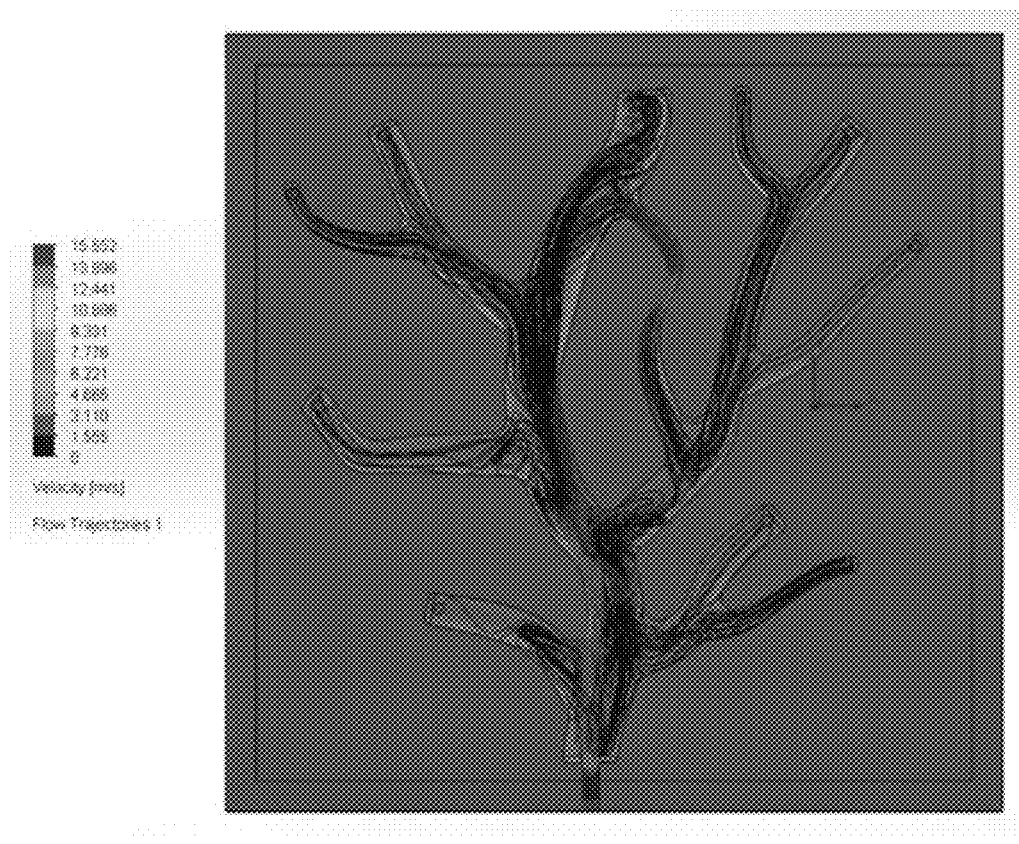
FIG. 9F is a fluid flow simulation for velocity in blood vessel branches.
Figure 10A:
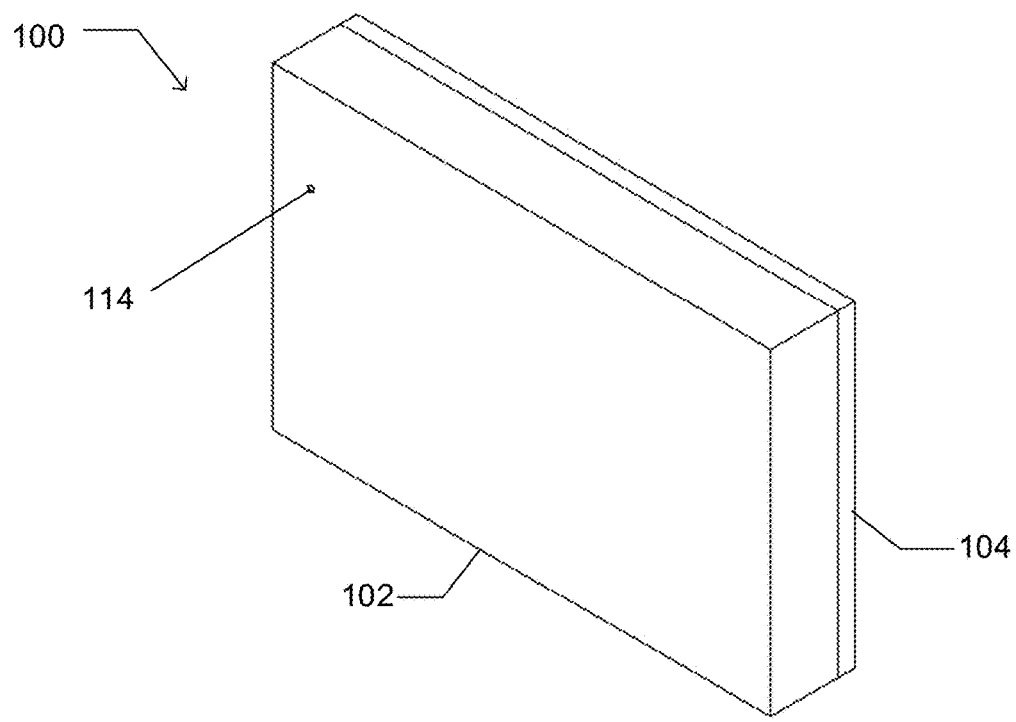
FIG. 10A is an example assembly fora capillary bed injection mold.
Figure 10B:
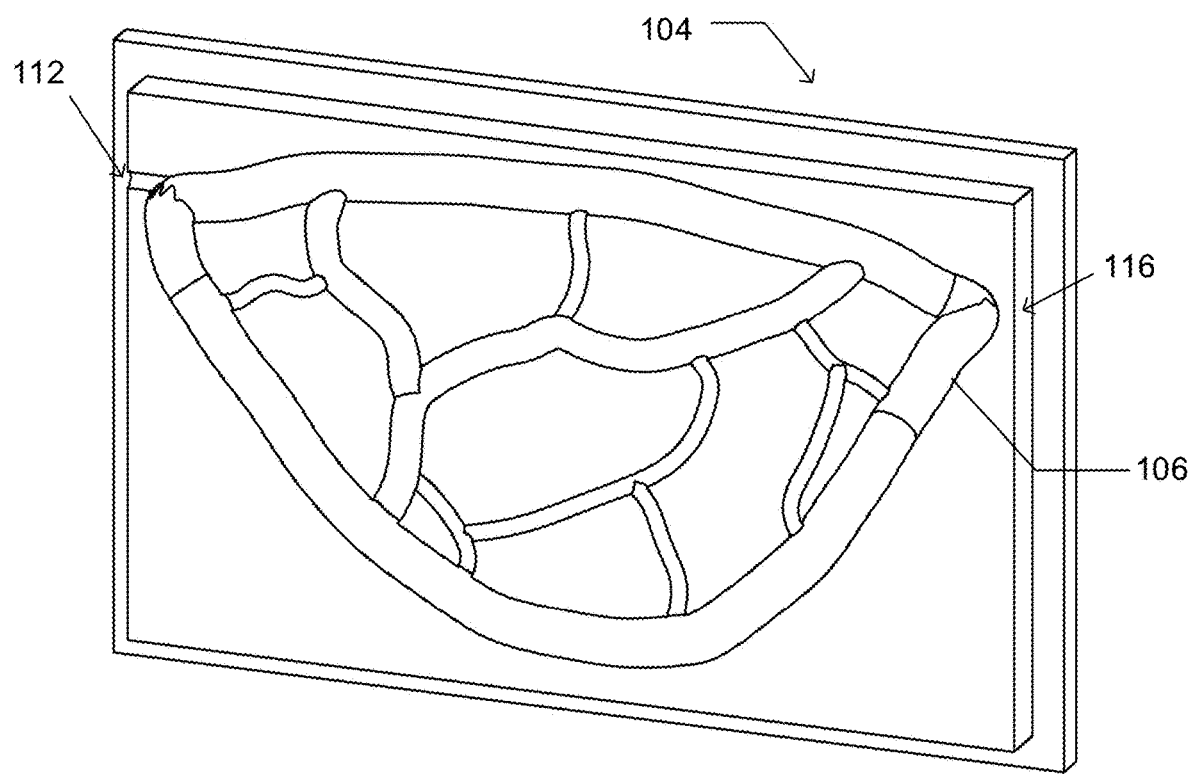
FIG. 10B is an example bottom portion of a capillary bed injection mold.
Figure 10C:
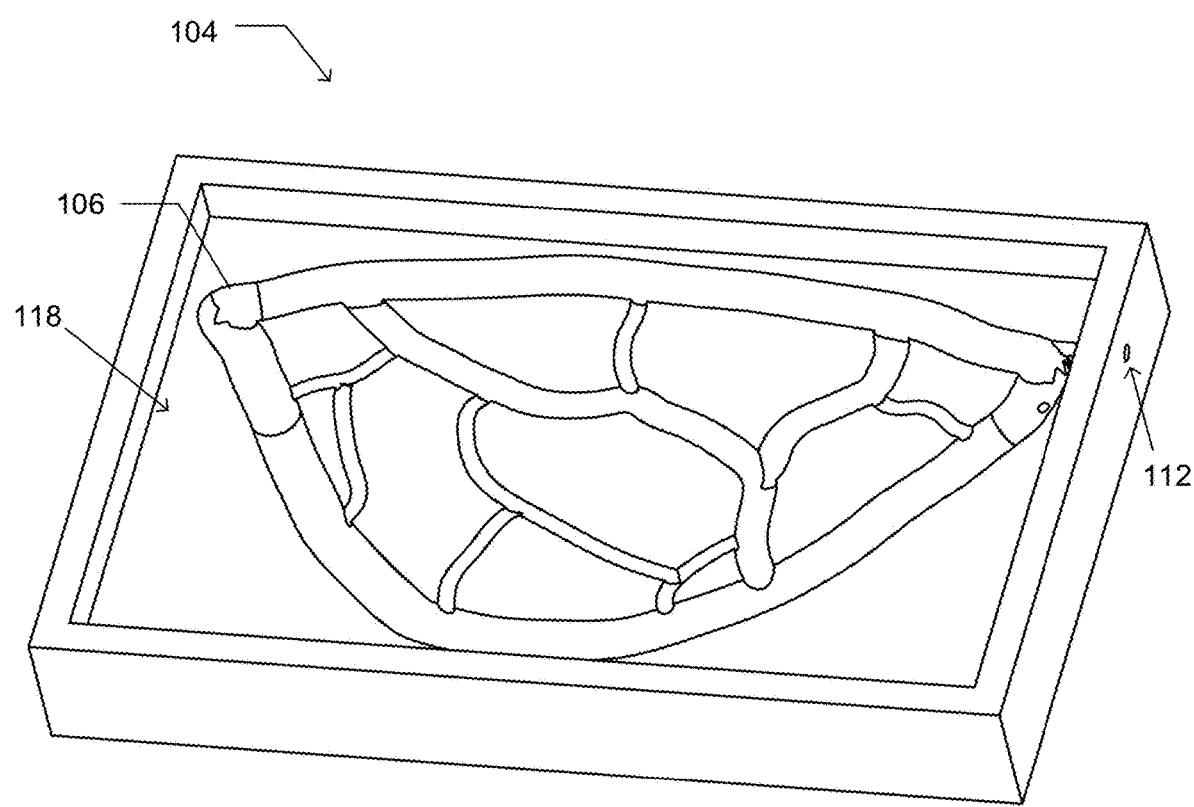
FIG. 10O is an example top portion of a capillary bed injection mold.
FIG. 10D is a fluid flow simulation for pressure in a capillary bed injection mold.
FIG. 10E is a fluid flow simulation for shear rate in a capillary bed injection mold.
FIG. 10F is a fluid flow simulation for velocity in a capillary bed injection mold.
Figure 10D:
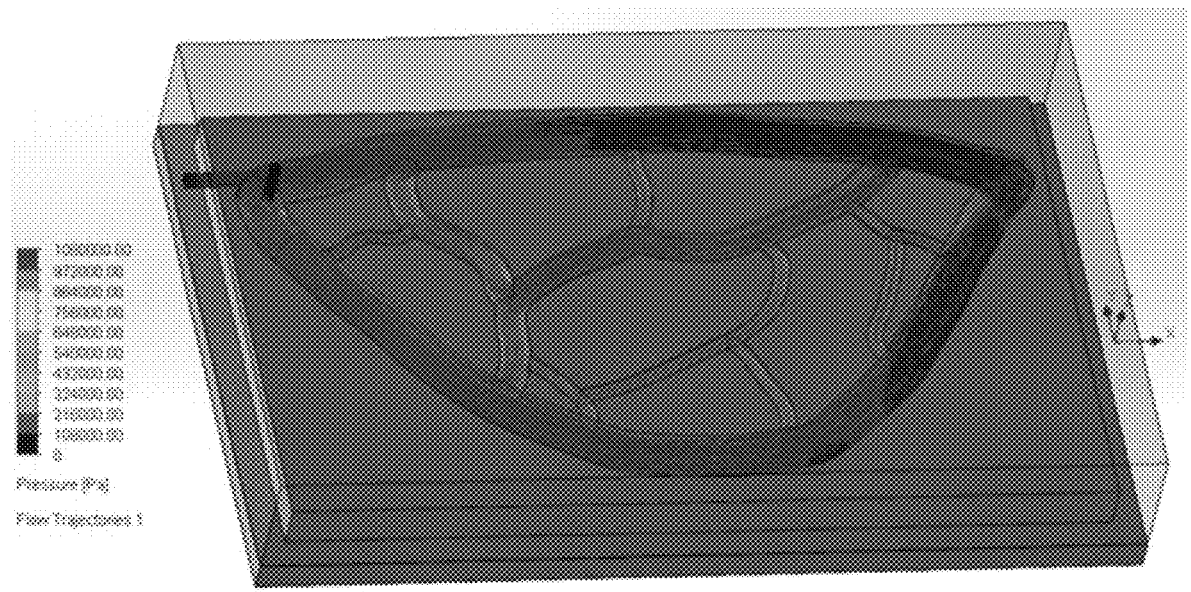
Figure 10E:
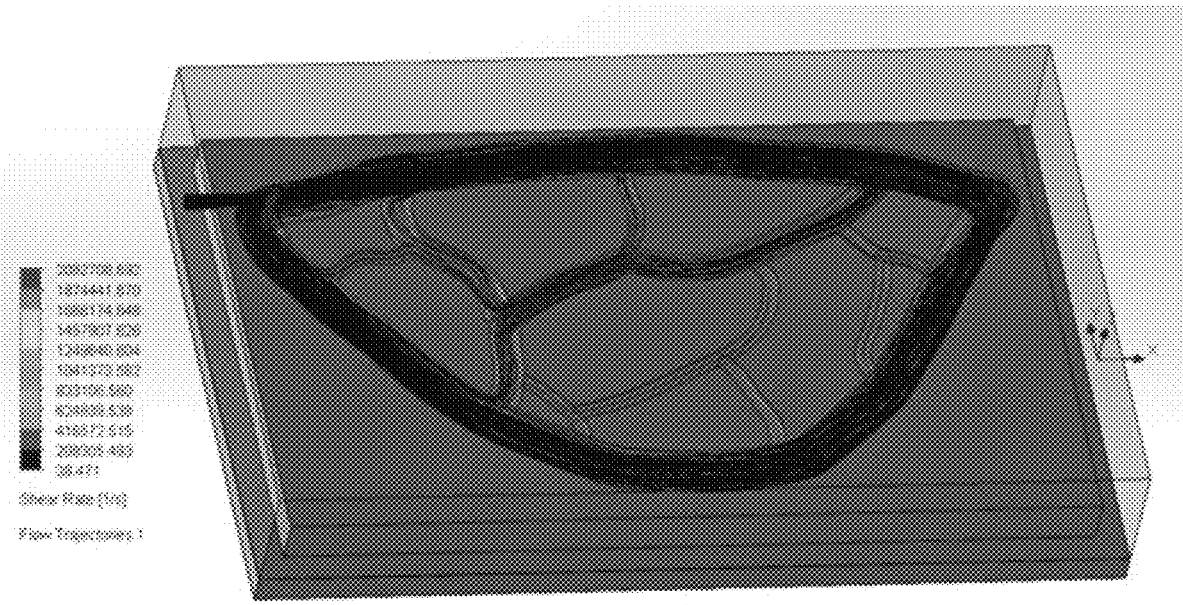
Figure 10F:
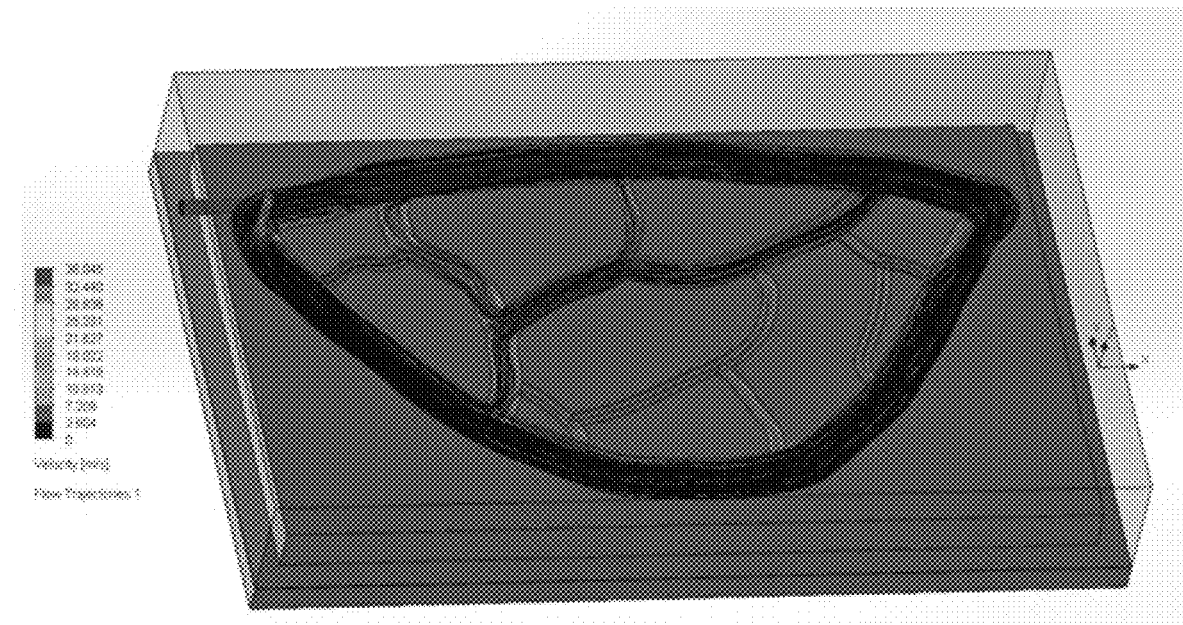
Figure 11A:
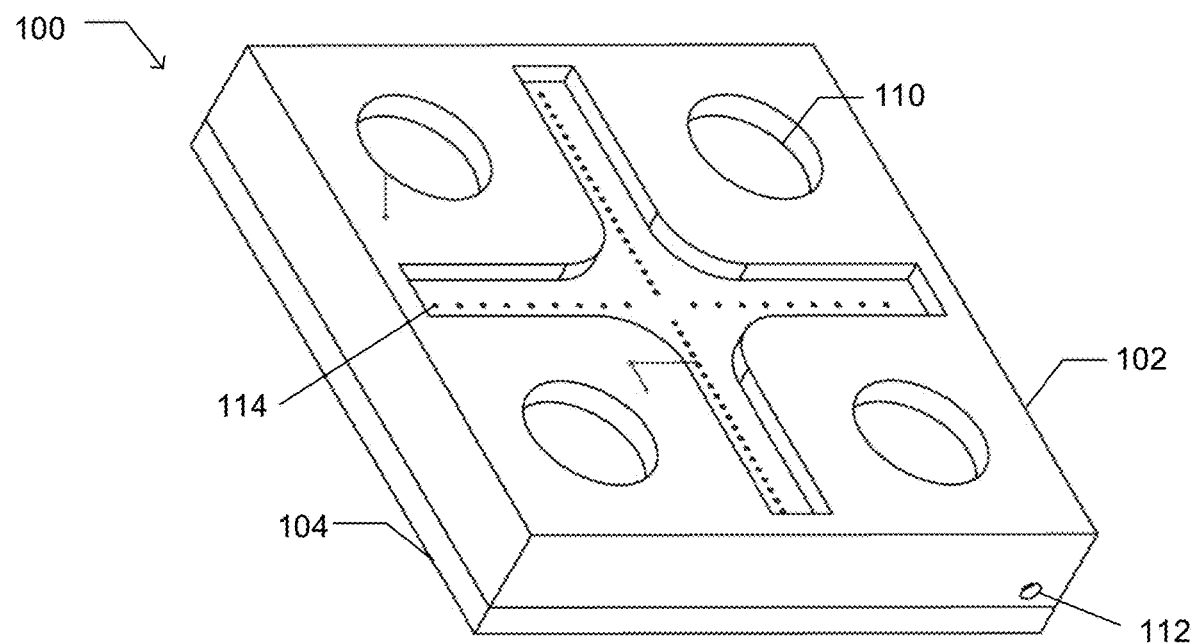
FIG. 11A is an example assembly for a human scale spiral injection mold.
Figure 11B:
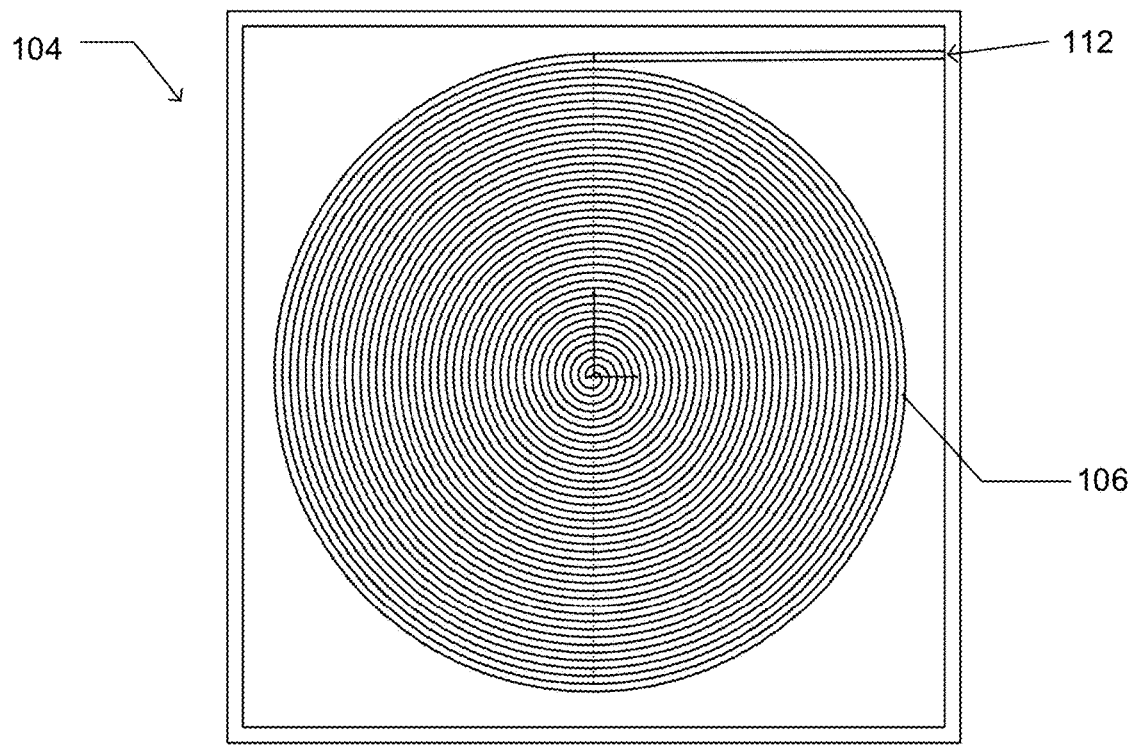
FIG. 11B is an example bottom portion of a human scale spiral injection mold.
Figure 11C:
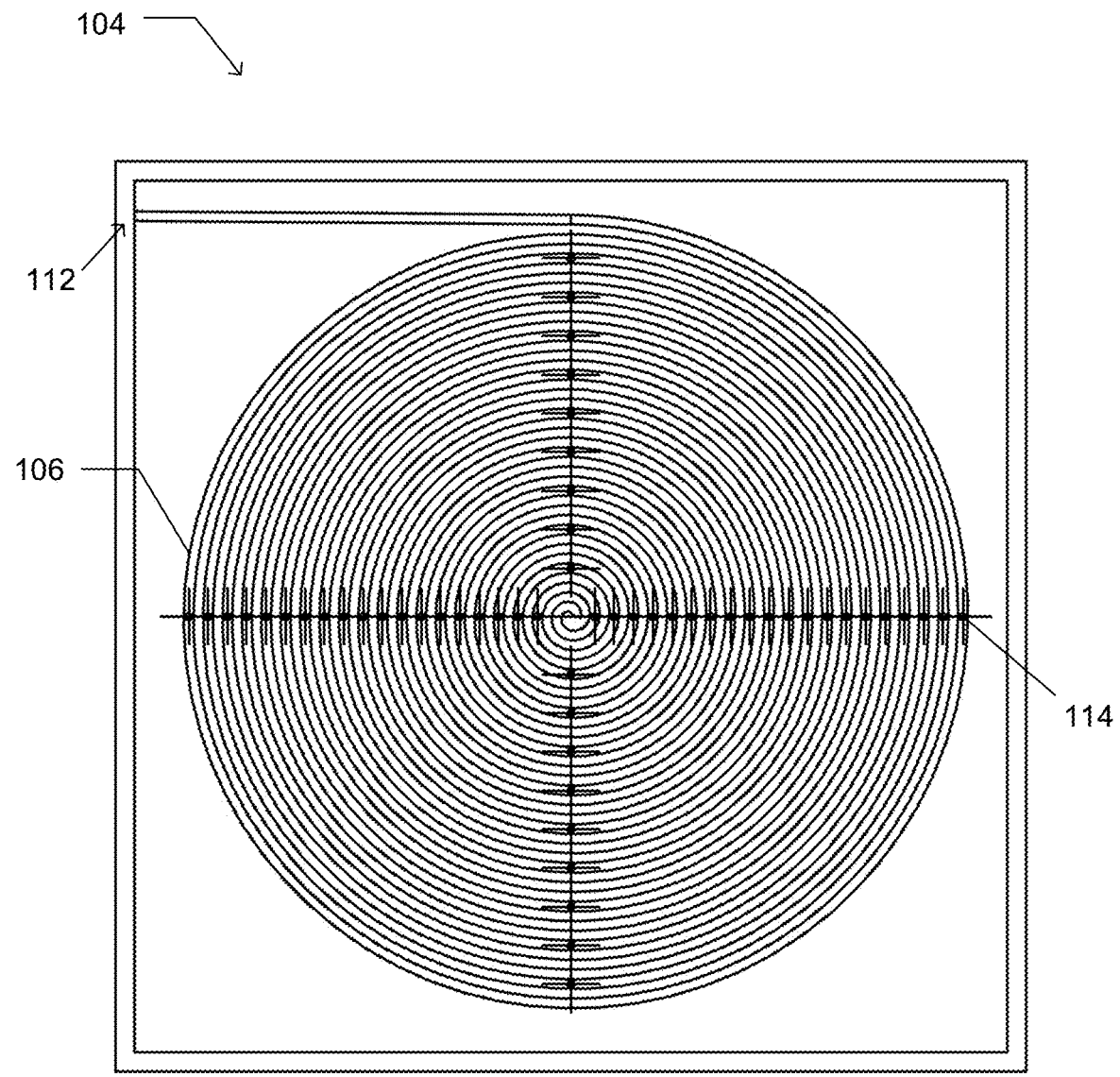
FIG. 11C is an example top portion of a human scale spiral injection mold.
Figure 11D:
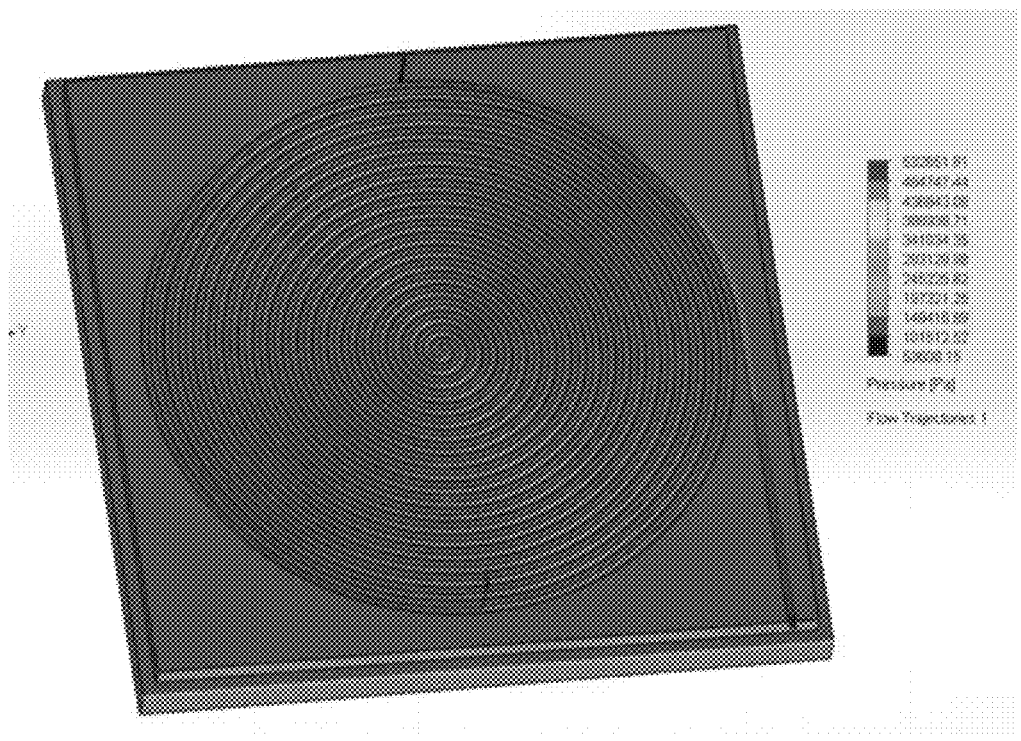
FIG. 11D is a fluid flow simulation for pressure in a human scale spiral injection mold.
Figure 11E:
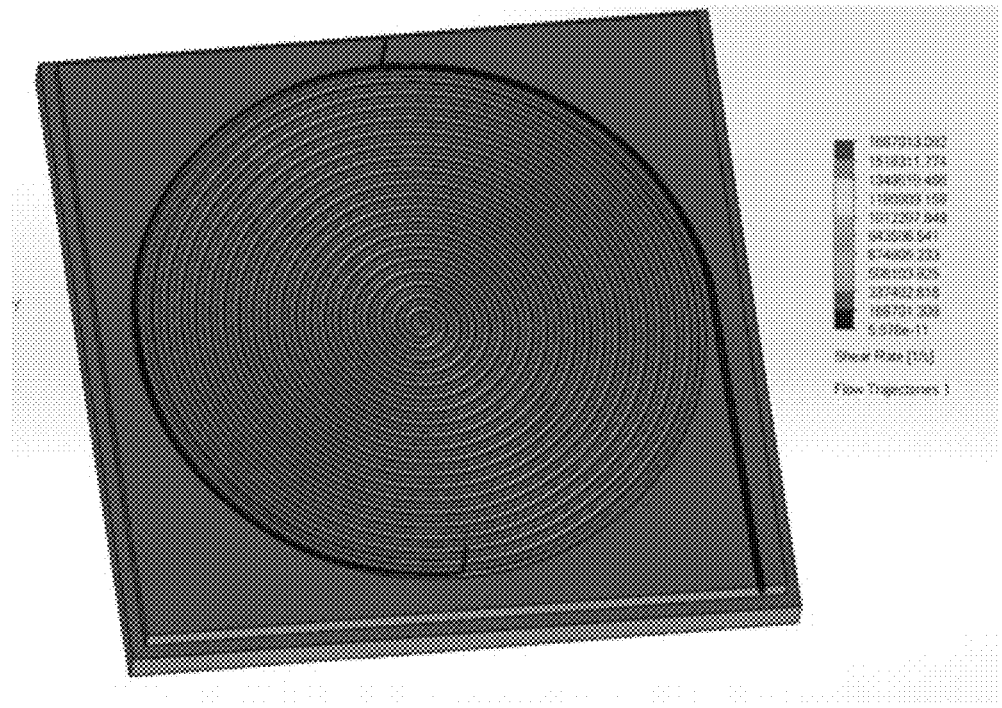
FIG. 11E is a fluid flow simulation for shear rate in a human scale spiral injection mold.
Figure 11F:
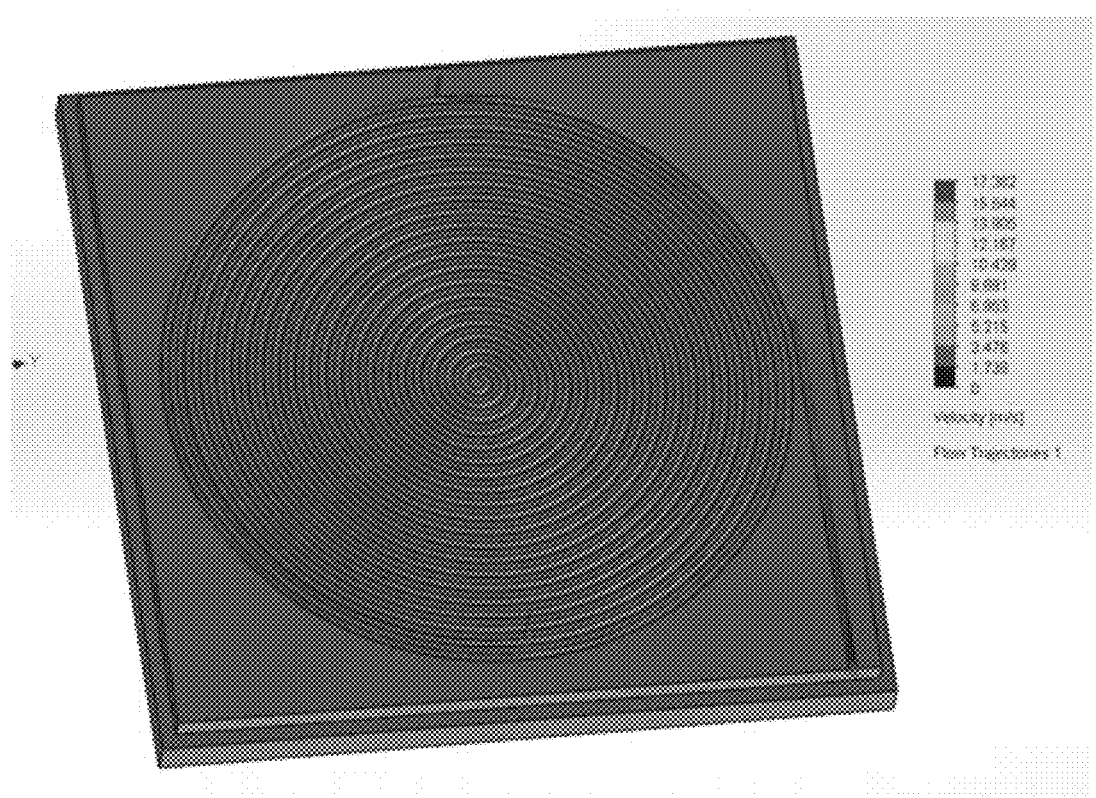
FIG. 11F is a fluid flow simulation for velocity in a human scale spiral injection mold.
Figure 12A:
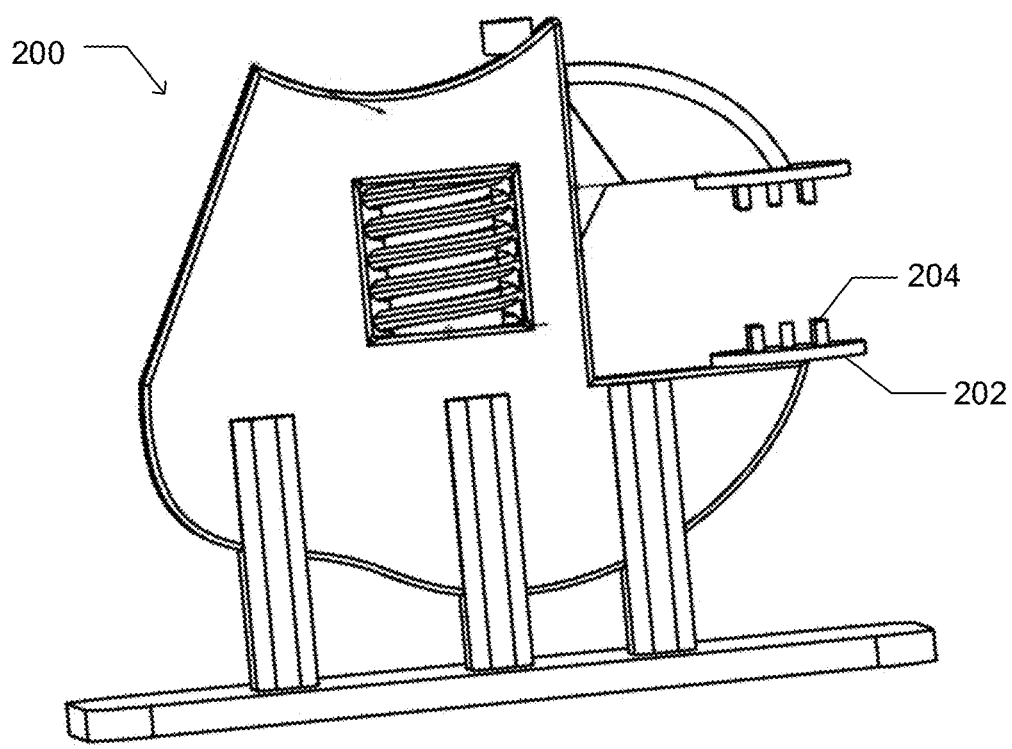
FIG. 12A is an example horizontal adjustable clamp.
Figure 12B:
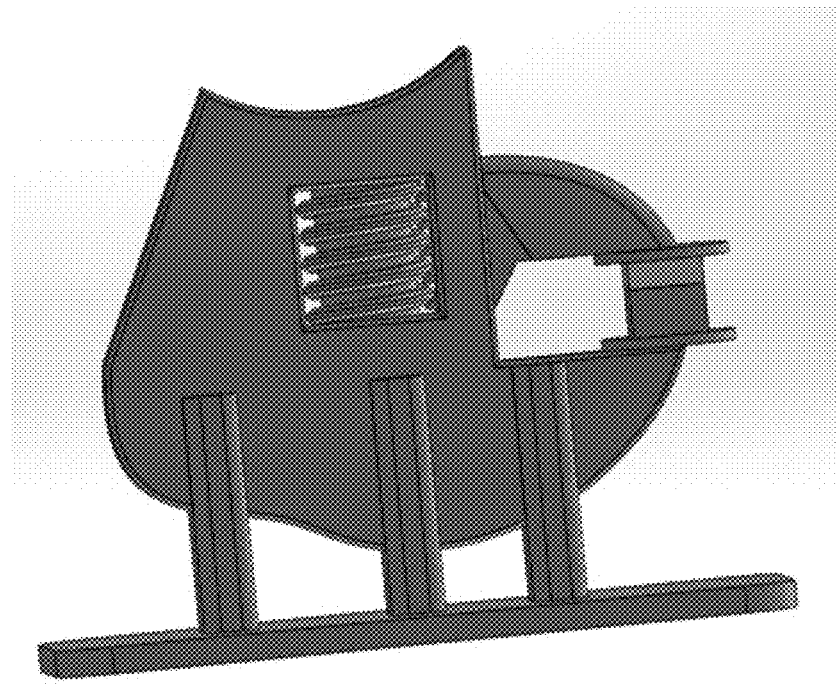
FIG. 12B is an example horizontal adjustable clamp with an injection mold device attached.
Figure 13A:
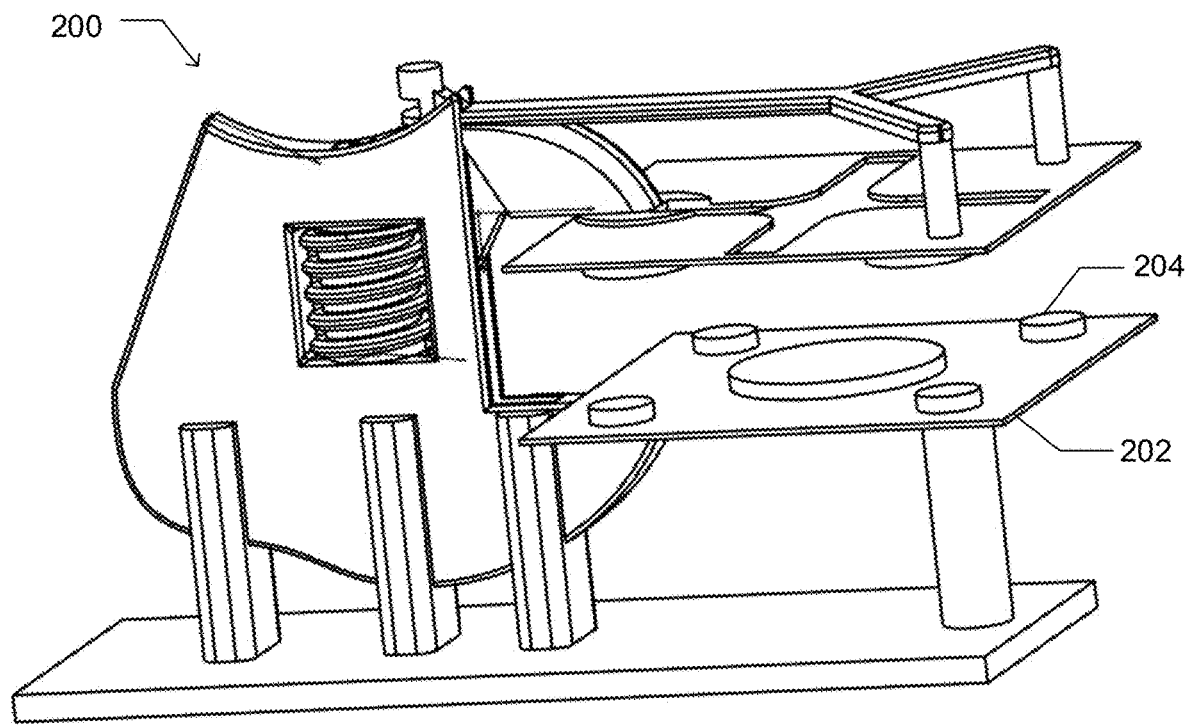
FIG. 13A is an example human scale adjustable clamp.
Figure 13B:
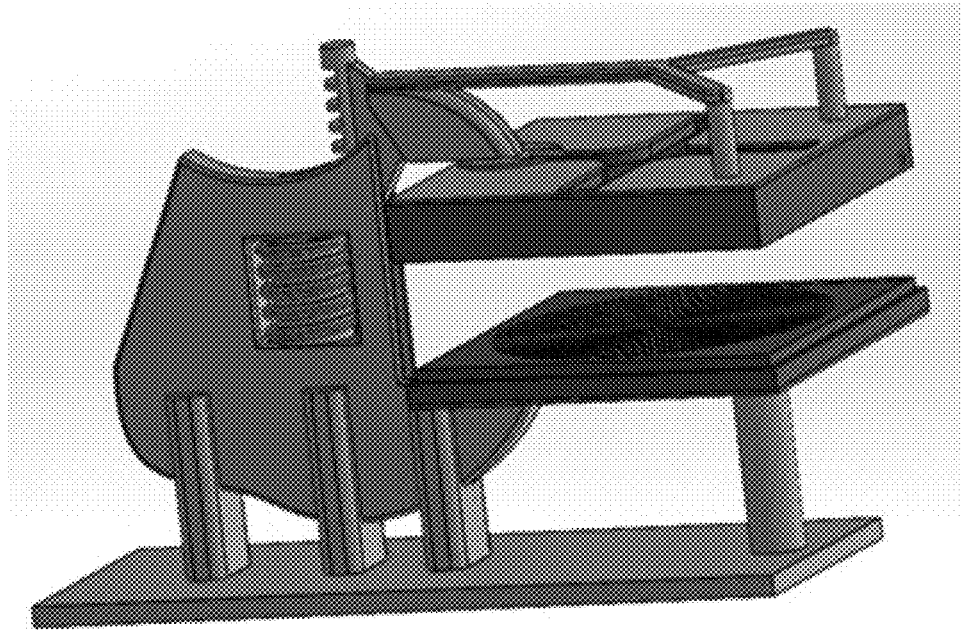
FIG. 13B is an example human scale adjustable clamp with a human scale injection mold attached.

In various examples, the channel or channels 106 in the top portion 102, middle portion 108, and/or bottom portion 104 of the injection mold device 100 may have a diameter of about 100 µm, 150 µm, 200 µm, 250 µm, 300 µm, 350 µm, 400 µm, 450 µm, 500 µm, 550 µm, 600 µm, 650 µm, 700 µm, 750 µm, 800 µm, 850 µm, 900 µm, 950 µm, 1000 µm, 1500 µm, 2000 µm, 2500 µm, 3000 µm, or any range between these values. In some examples, the one or more channels may have a diameter of about 0.5 mm, about 1 mm, about 2 mm, or about 3 mm. The channel 106 may vary in diameter. For example, the diameter of the channel 106 may be wider near the inlet 112 than throughout the rest of the top portion 102 or bottom portion 104, as seen in FIGS. 6B-6C. In other examples, the diameter may vary throughout the top portion or bottom portion to mimic vasculature, as seen in FIGS. 9B-9C and 10B-10C.

In various examples, the top portion 102, middle portion 108, and/or bottom portion 104 of the injection mold device 100 may have a length and/or width of about 10 mm, about 15 mm, about 20 mm, about 25 mm, about 30 mm, about 35 mm, about 40 mm, about 45 mm, about 50 mm, or any range between these values.

III. Macroencapsulation Kit

Further provided herein is a macroencapsulation kit that includes the hydrogel components, as well as the injection mold device. In an example, the mold and the hydrogel components may be provided as an off-the-shelf kit, deployable in the clinic by a trained user. In an example, the macroencapsulation kit may be readily manufactured, shipped, and stored until time of use in the clinic. For example, when a cadaveric donor organ source of cells (e.g. islets) becomes available, the macroencapsulation kit may be used to fabricate hydrogel macroencapsulation devices at the transplant recipient bedside under aseptic conditions.

In some examples, the kit may further include a syringe and/or clamp to secure the injection mold. The hydrogel-cell mixture may be injected into the injection mold using the syringe, mold, and clamp. After a prescribed amount of time, the injection mold device may be released from the clamp, opened, and the hydrogel macroencapsulation device transferred to the patient.

Injection molding readily scales for high-throughput manufacturing of products. Methods to generate large scale stem cell-derived cell sources are in development. As such, this cell technology may be paired with the injection molding hydrogel encapsulation strategy within a high-throughput and automated manufacturing process. This would enable large-scale manufacturing of devices to treat disease, such as insulin-dependent diabetic patients.

EXAMPLES

Example 1: Finite Element Modeling Macroencapsulation Device Design and Device Prototyping Devices were designed using finite element modeling of oxygen distribution throughout the device to determine optimal structure for encapsulated cell long-term viability and function. 3D printed injection molds were designed, fabricated, and tested for feasibility of facile use in the clinic. Concurrently, a material library was evaluated for use as a biostable synthetic encapsulation hydrogel with adequate crosslinking time for use in injection molding. Predictive modeling of macroencapsulation device transport resulted in device designs that maximize encapsulated islet viability and function, while 3D printing enabled facile and rapid prototyping of injection molds.

Figure 1B:
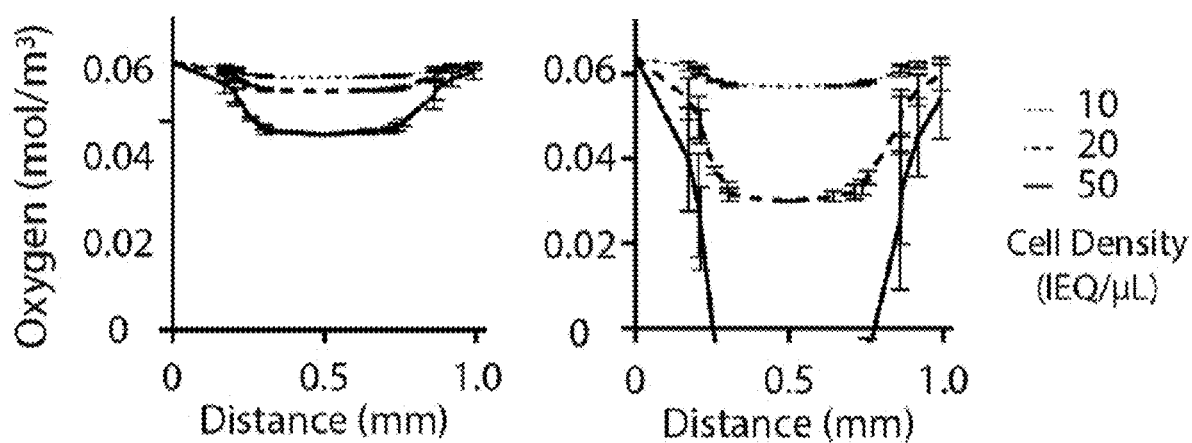
FIG. 1B shows oxygen concentration versus distance for different cell densities using the device of FIG. 1A.
Figure 4A:
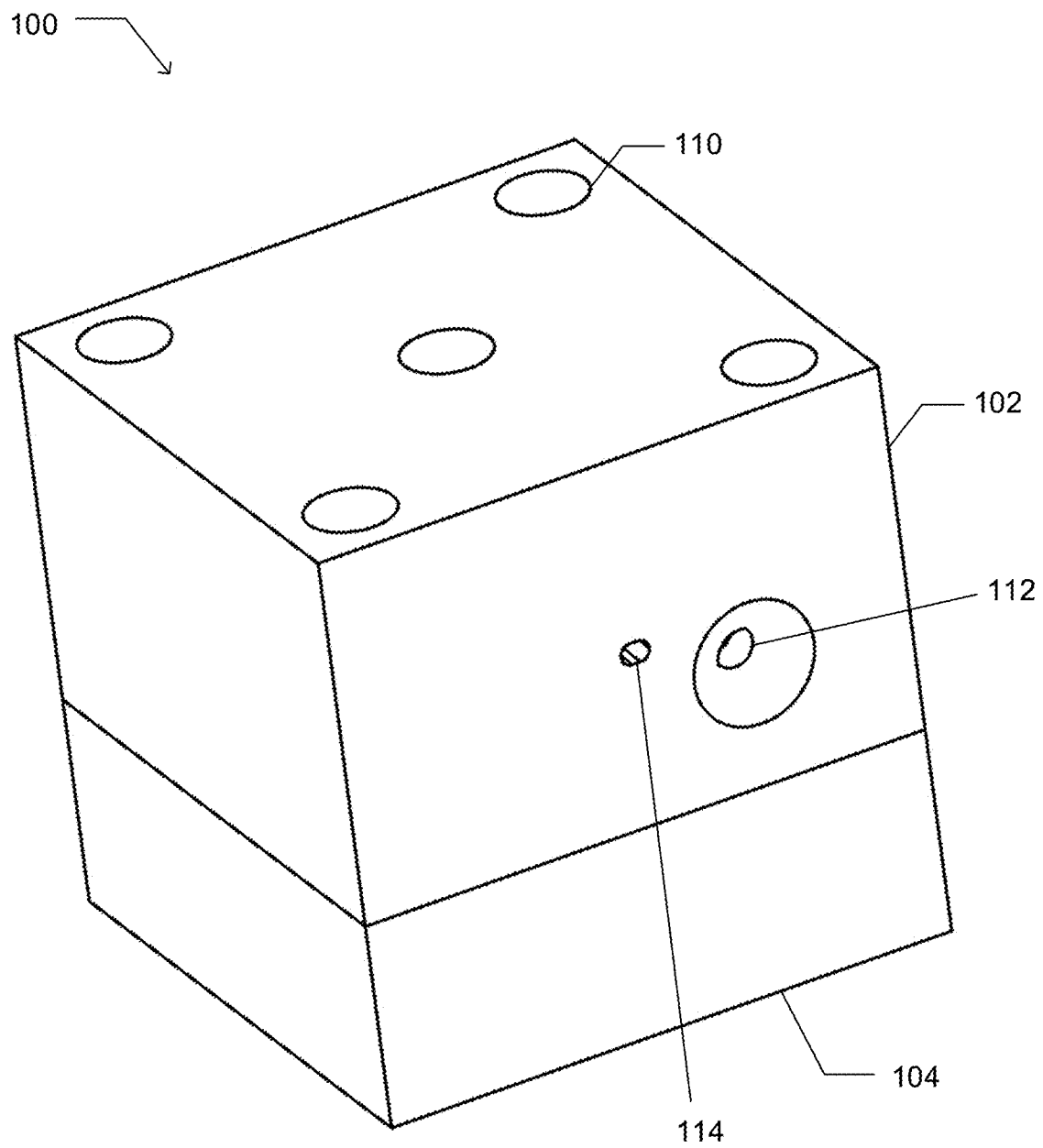
FIG. 4A is an example assembly for a 1 mm diameter spiral embodiment of the injection mold.
Figure 4B:
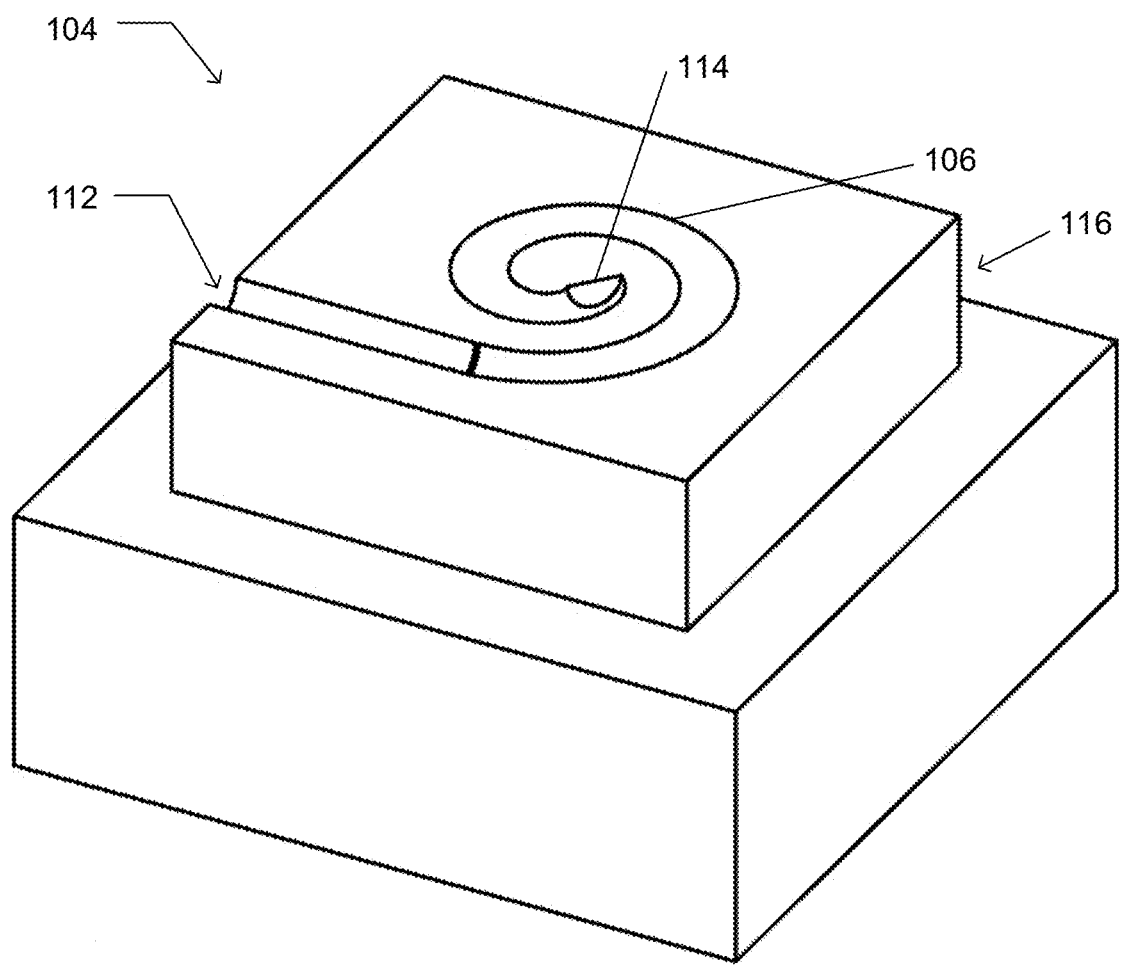
FIG. 4B is an example bottom portion of an assembly for a 1 mm diameter spiral embodiment of the injection mold.
Figure 4C:
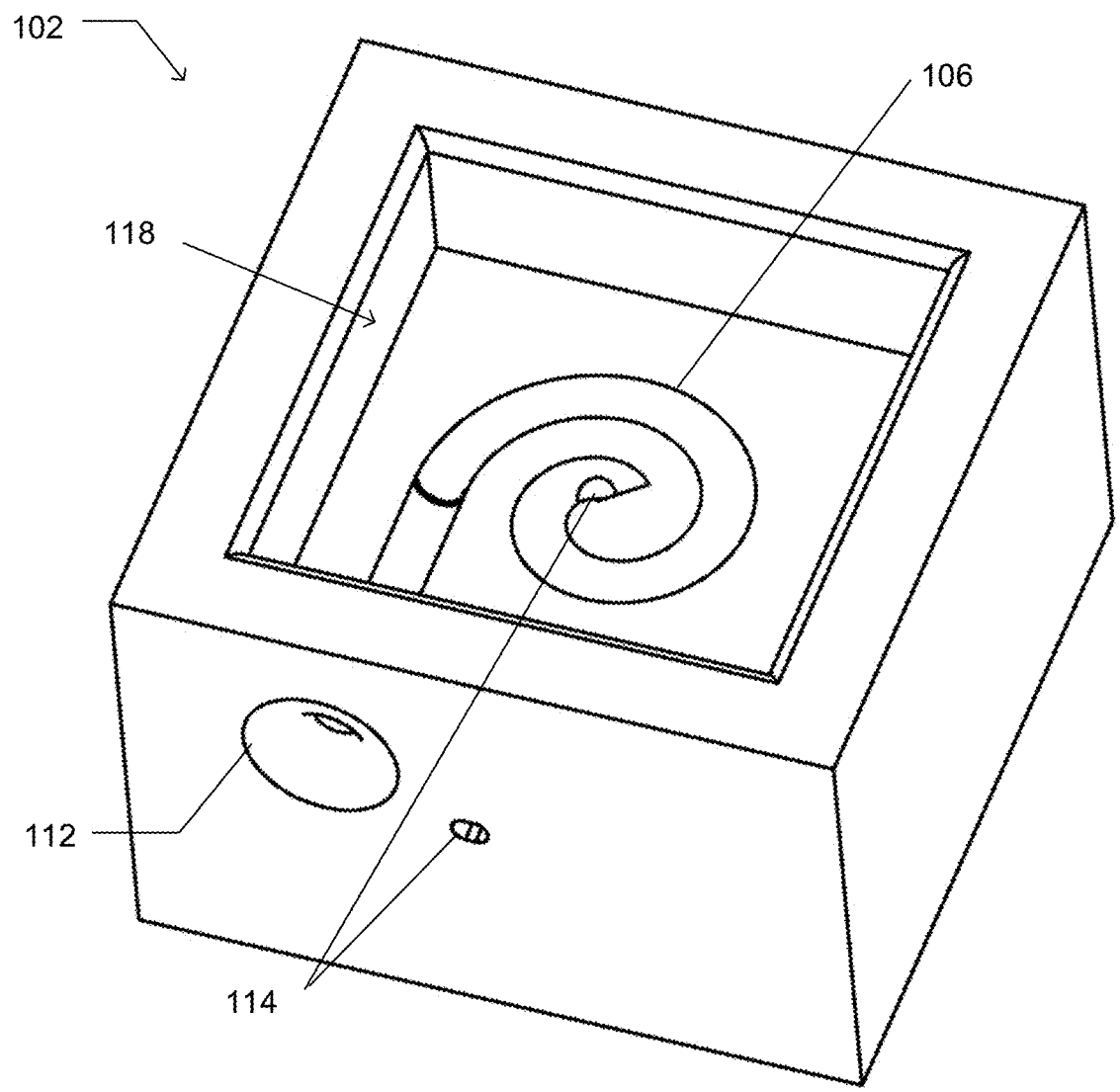
FIG. 4C is an example top portion of an assembly for a 1 mm diameter spiral embodiment of the injection mold.
Figure 4D:
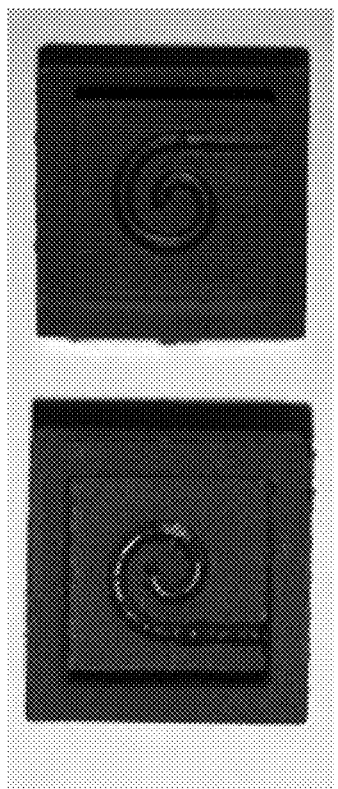
FIG. 4D shows an injection mold with an alginate hydrogel inside the mold.
Figure 4E:
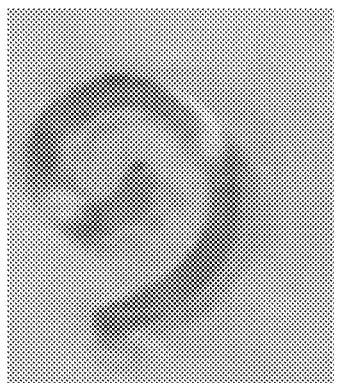
FIG. 4E shows the hydrogel of FIG. 4D extracted from the injection mold.
Figure 4F:
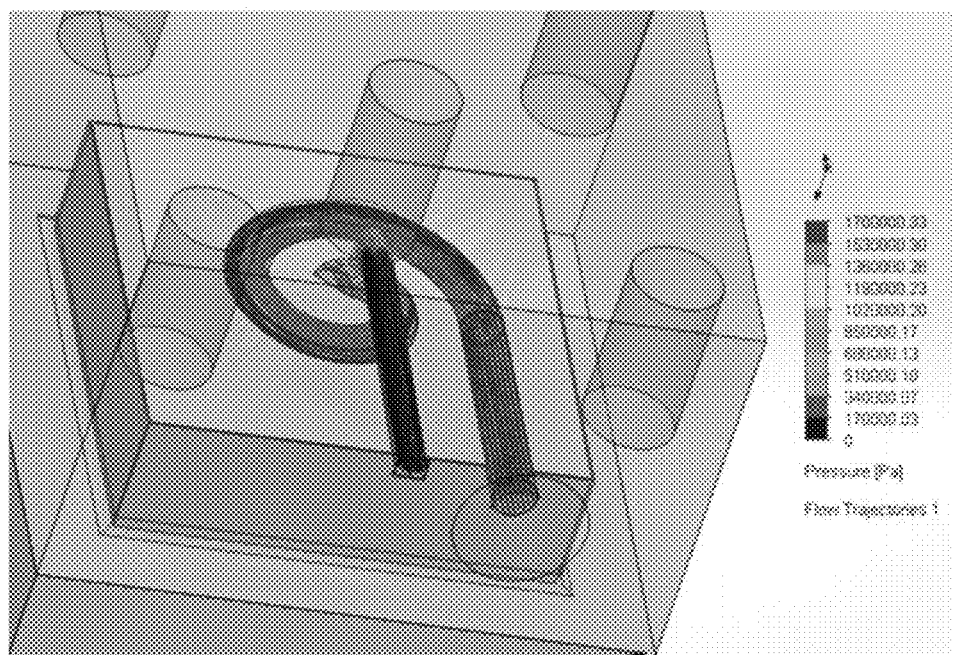
FIG. 4F is a fluid flow simulation for pressure in a 1 mm diameter spiral embodiment of the injection mold.
Figure 4G:
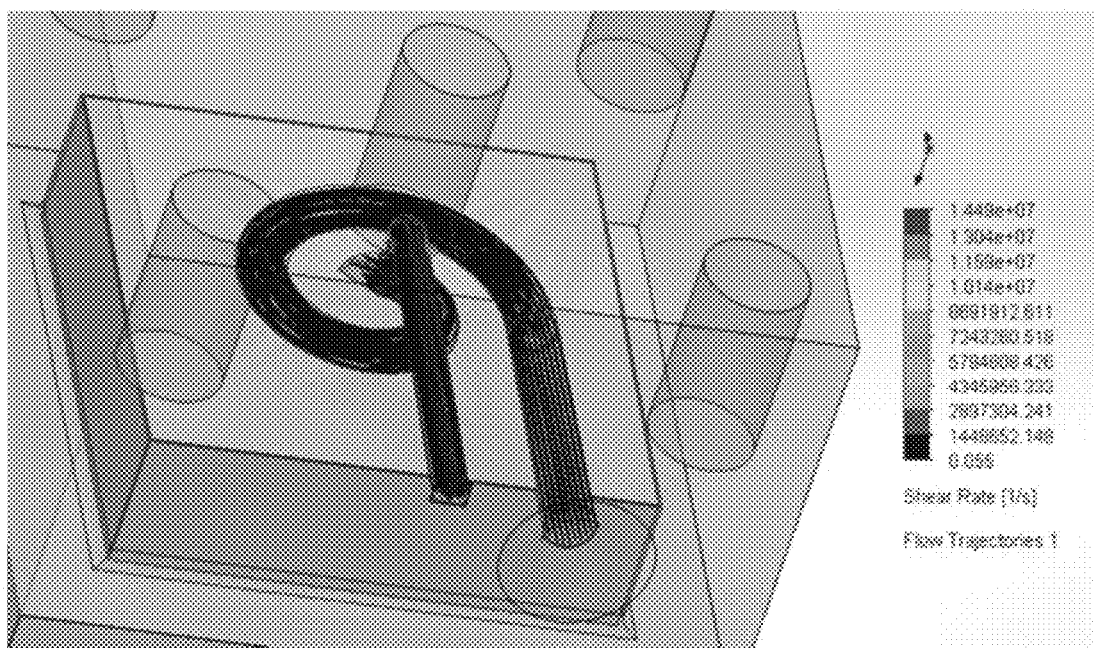
FIG. 4G is a fluid flow simulation for shear rate in a 1 mm diameter spiral embodiment of the injection mold.
Figure 4H:
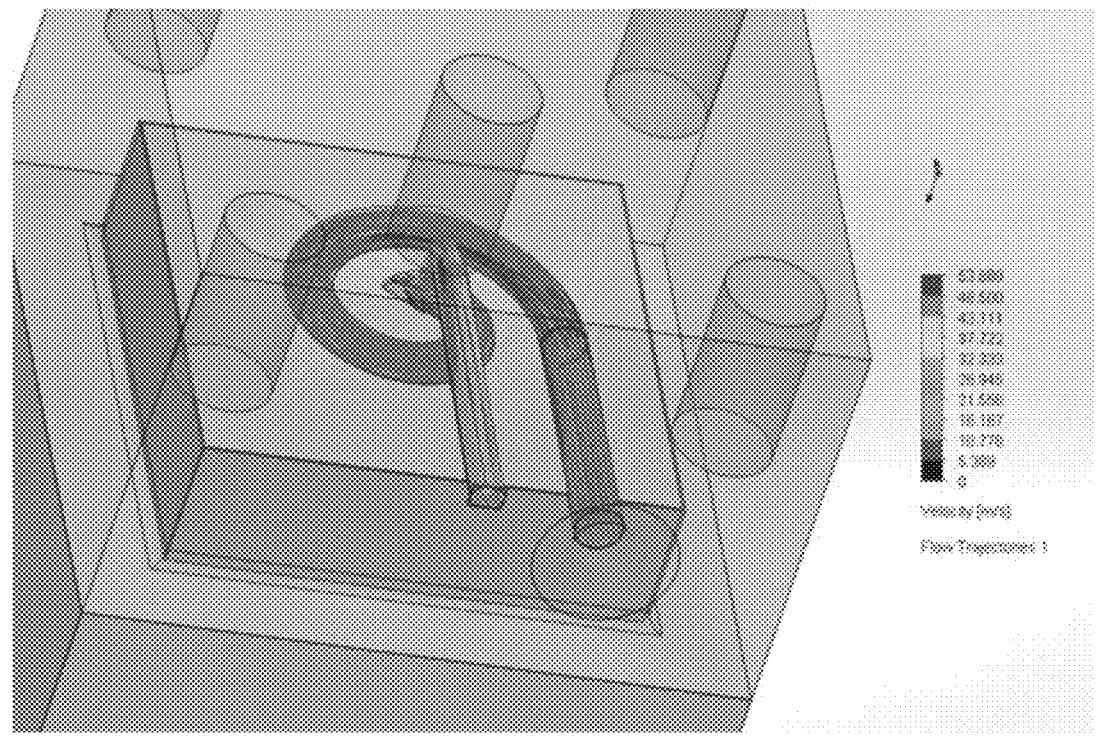
FIG. 4H is a fluid flow simulation for velocity in a 1 mm diameter spiral embodiment of the injection mold.
Figure 5A:
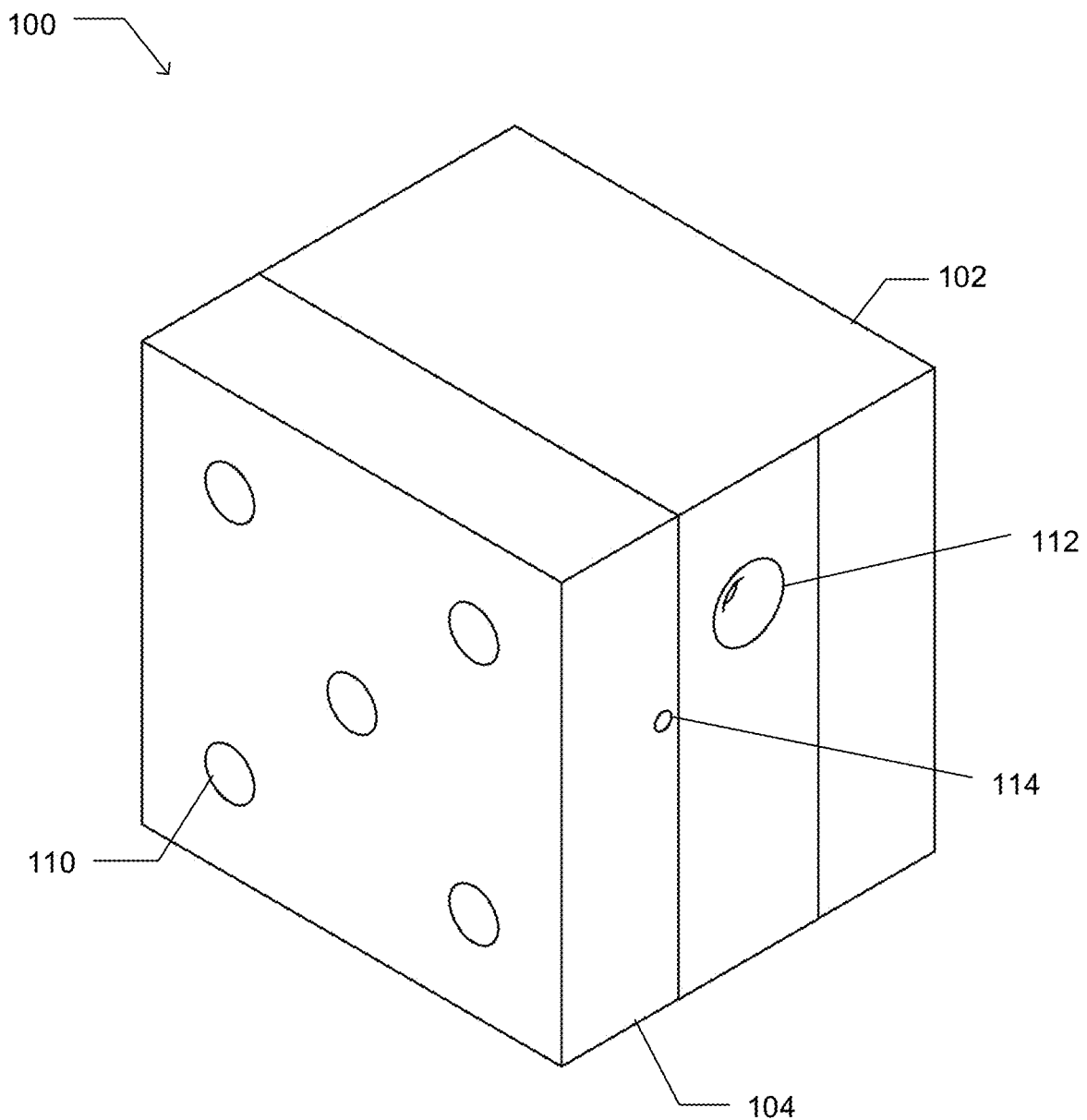
FIG. 5A is an example assembly for a 2 mm diameter spiral embodiment of the injection mold.
Figure 5B:
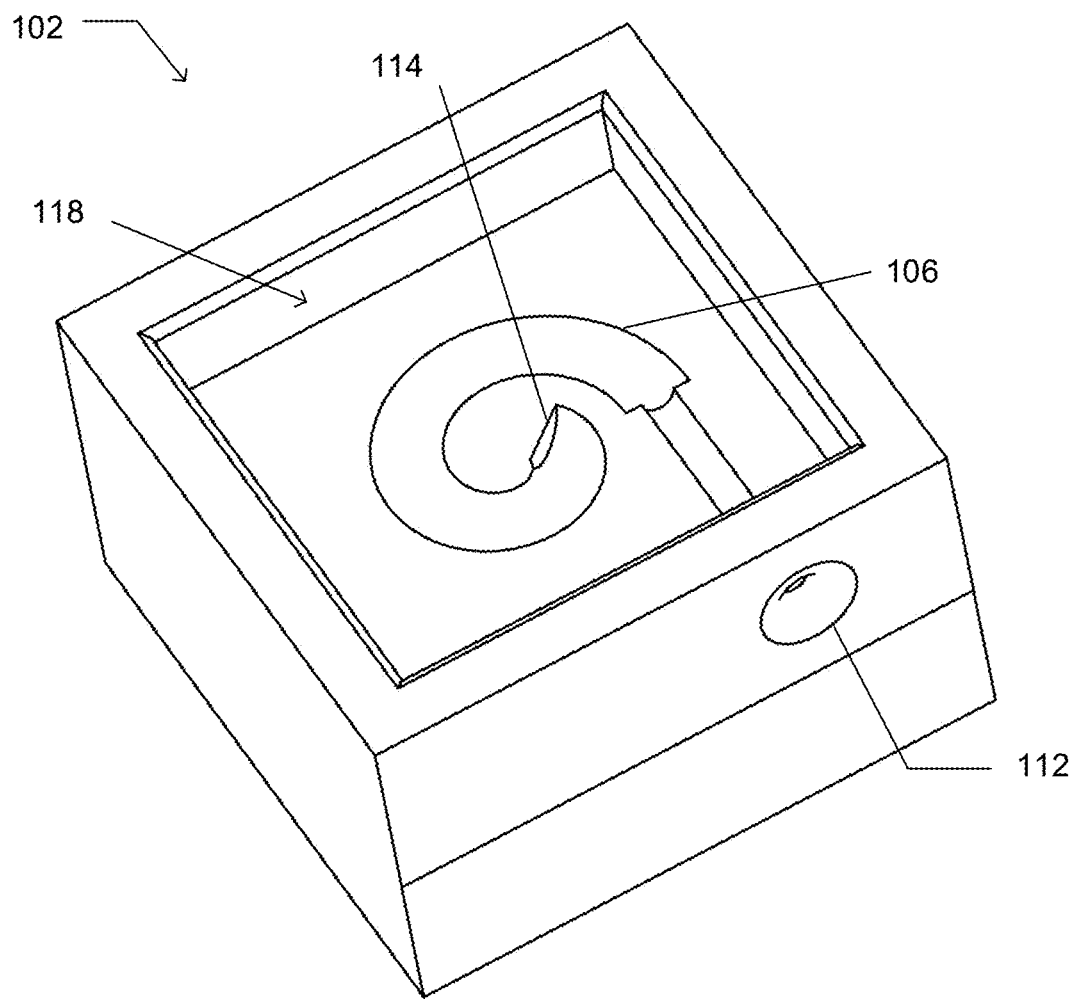
FIG. 5B is an example top portion of an assembly for a 2 mm diameter spiral embodiment of the injection mold.
Figure 5C:
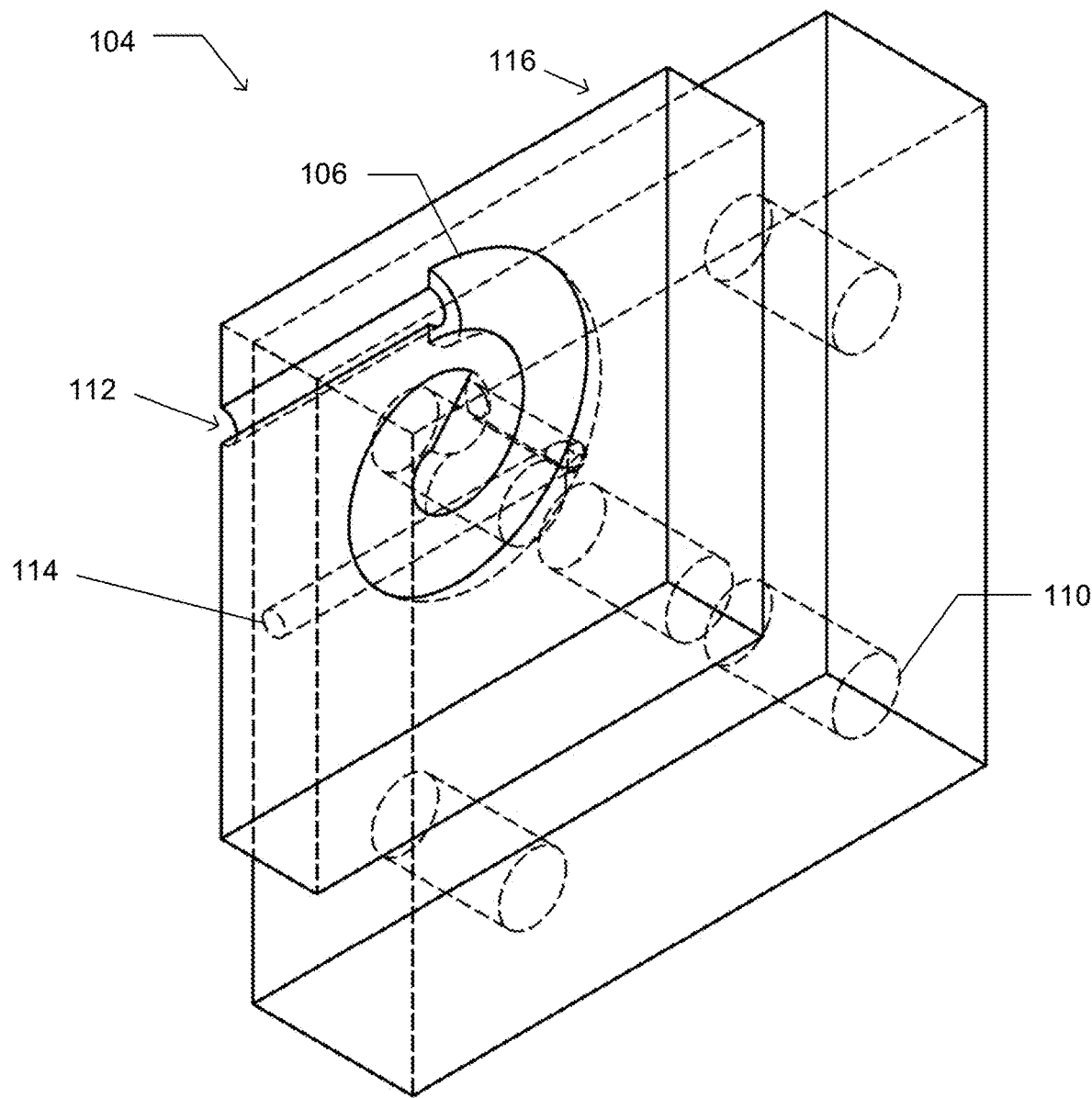
FIG. 5C an example bottom portion of an assembly for a 2 mm diameter spiral embodiment of the injection mold.
Figure 5D:
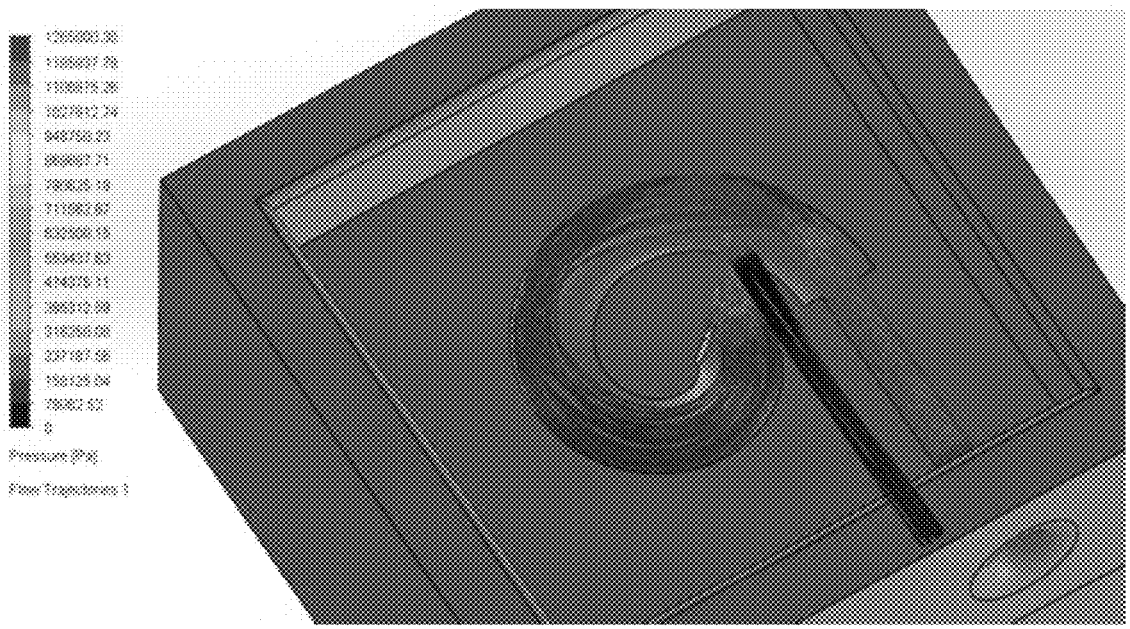
FIG. 5D is a fluid flow simulation for pressure in a 2 mm diameter spiral embodiment of the injection mold.
Figure 5E:
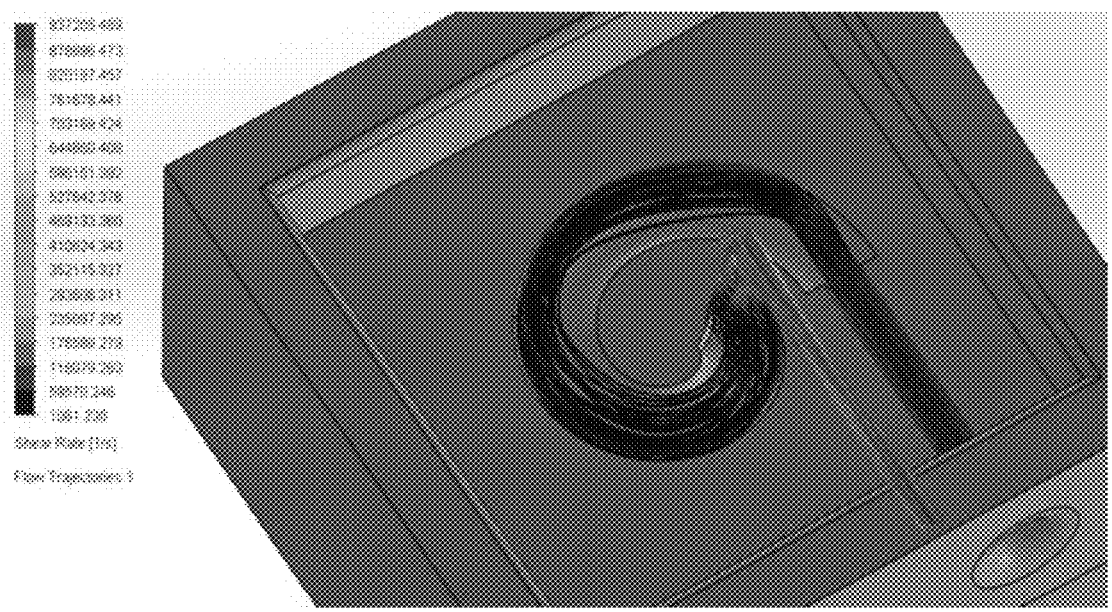
FIG. 5E is a fluid flow simulation for shear rate in a 2 mm diameter spiral embodiment of the injection mold.
Figures 5F, 5G:
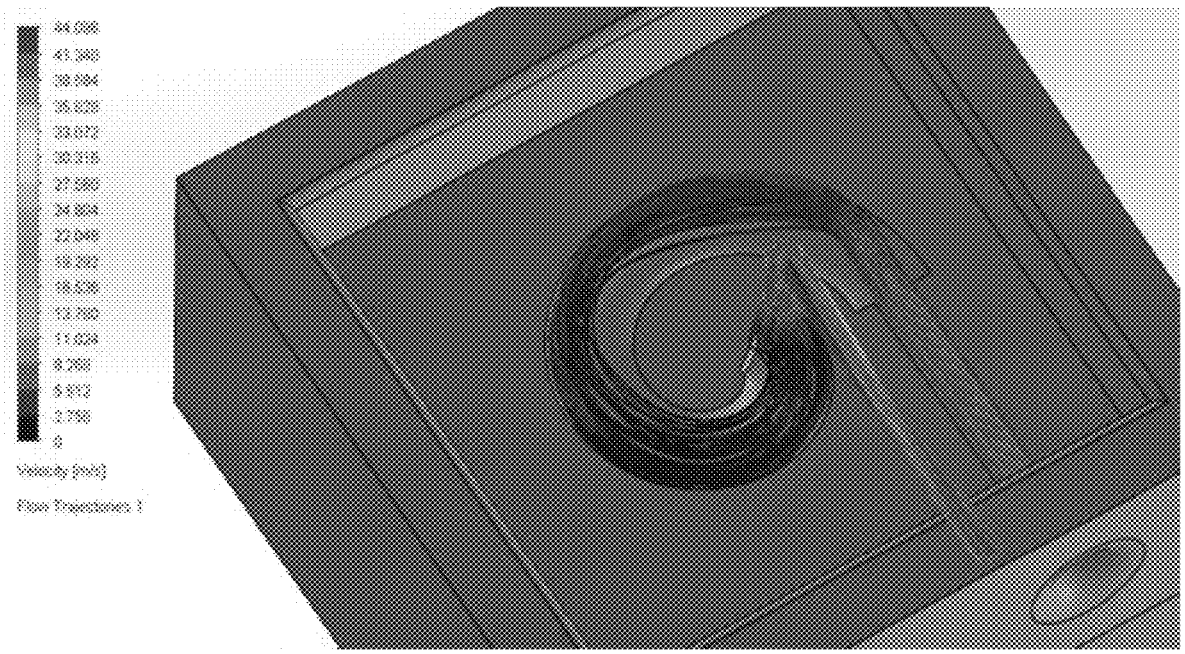
FIG. 5F is a fluid flow simulation for velocity in a 2 mm diameter spiral embodiment of the injection mold.
FIG. 5G shows both a bottom and top portion of an injection mold device for 2 mm diameter spiral, made out of flexible resin.
Figure 5H:
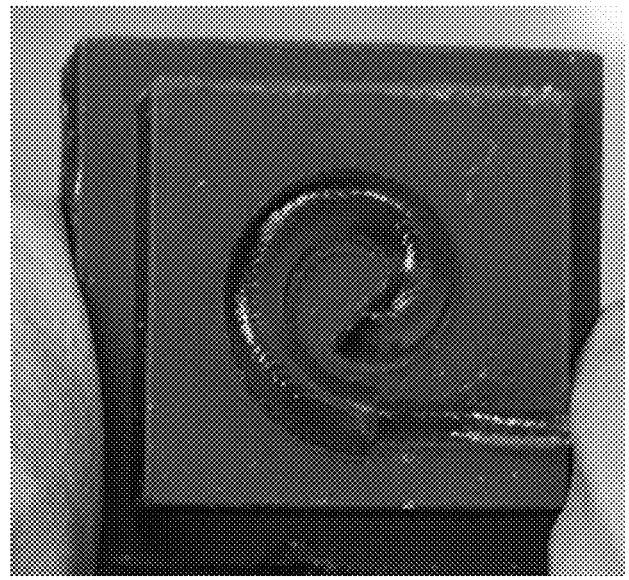
FIG. 5H shows an example working injection mold with an agarose based hydrogel inside the mold.
Figure 5I:
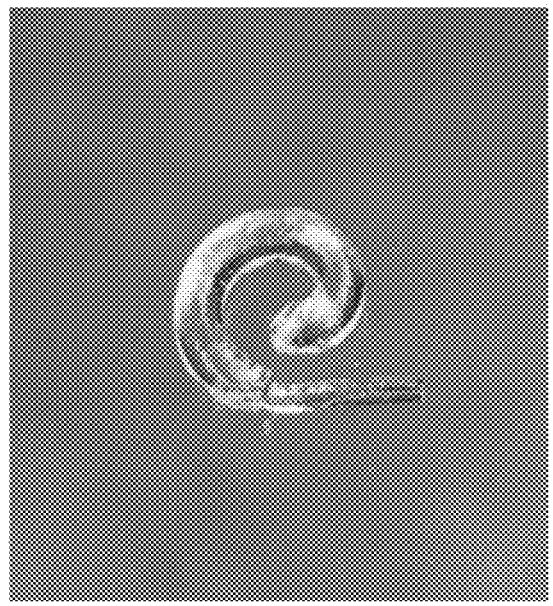
FIG. 5I shows an agarose hydrogel extracted from the example injection mold device of FIG. 5H.
Figure 5J:
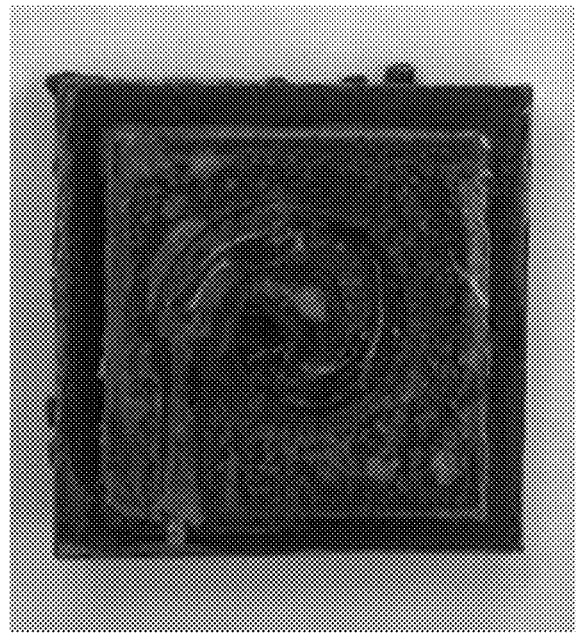
FIG. 5J shows an example working injection mold with an alginate based hydrogel inside the mold.
Figure 5K:
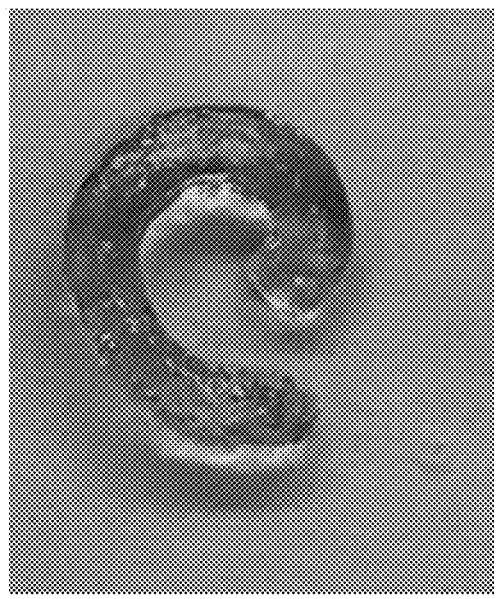
FIG. 5K shows an alginate hydrogel extracted from the injection mold device of FIG. 5J.

Rather than the typical trial-and-error approach to device design, an in silico evaluation of device oxygenation prior to fabrication and testing in vitro streamlined prototyping and improved macroencapsulated islet function and viability. Alternative geometries that aim to minimize oxygen diffusion distances and eliminate suboptimal oxygen gradients include geometries such as the spiral and crimped sheet, as illustrated in FIGS. 1-3. Regions of poor oxygenation within the device are likely modulated by cell density within the device. Modeling was used to predict the maximal cell density per device while still maintaining cell viability. Optimal cell densities (about 1 IEQ/µL and about 50 IEQ/µL) were derived for each device to determine the ultimate scale of devices and their practicality for facile translation to the clinic.

3D printing technology enabled rapid prototyping of device molds for injection-molded hydrogel designs. A stereolithography 3D printer (Formlabs) was used to print molds in Elastic resin, a resin with physical properties comparable to poly(dimethyl siloxane) (PDMS), an ideal material for injection molding hydrogels. Example 3D models are pictured in FIGS. 4A-11F. The use of in situ injection molding for macroencapsulation device fabrication was advantageous over current encapsulation techniques in that no specialized equipment is required for fabrication in the clinic. 3D printed injection molds were designed and validated. 3D printing technology enabled rapid and cost-effective prototyping of devices, allowing for iterative determination of optimal design for use in the clinic.

Figure 18:
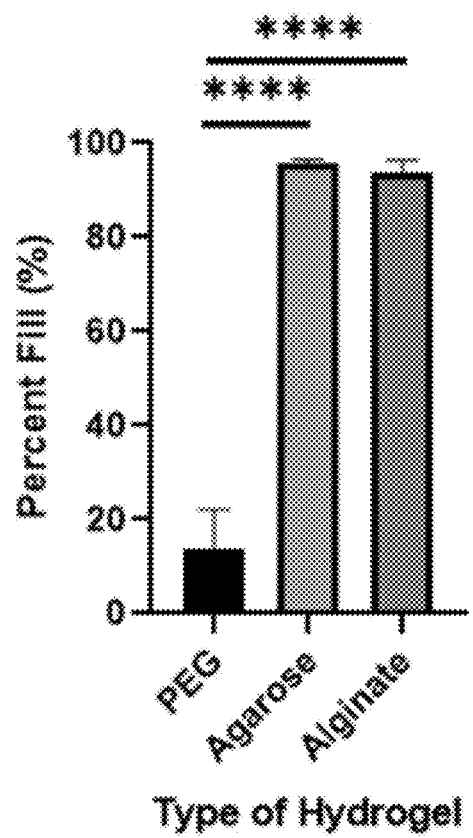
FIG. 18 shows the percent fill of an injection mold using PEG, agarose, and alginate based hydrogels.

FIG. 18 shows the percent fill of a 2 mm diameter injection mold using PEG, agarose, and alginate based hydrogels. Agarose and alginate based hydrogels filled the 2 mm diameter injection mold significantly more than a PEG based hydrogel.

Figure 17:
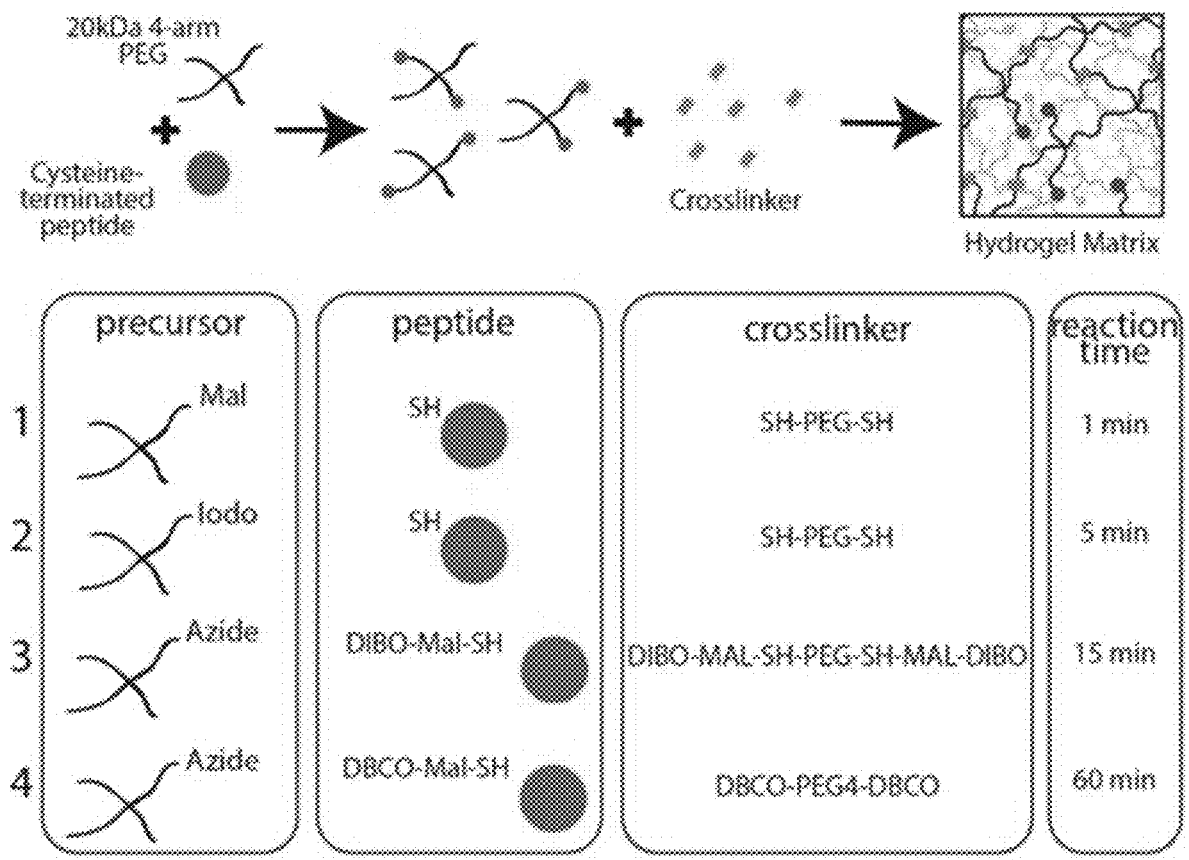
FIG. 17 shows example biocompatible and biorthogonal reaction schemes for material library testing. The general strategy entails a synthetic 4-arm PEG macromer precursor incubated with an adhesive ligand (RGD), prior to crosslinking with a short linker according to the reaction scheme. Each reaction scheme possesses a range of hypothesized reaction times.

Concurrently with injection mold optimization via 3D printing, a library of synthetic encapsulation materials were evaluated, selecting for candidates that are (1) of optimal biostability and (2) ideal crosslinking times for injection molding (~1-30 min). The collection of proposed reactive groups (FIG. 17) represent biorthogonal reactions, reactions with a high degree of specificity in physiological conditions, with the reported reaction times to meet the needs of the encapsulation strategy. As such, the kinetics of hydrogel crosslinking were evaluated, as well as the susceptibility of hydrogel platforms to common means of degradation in vivo (hydrolysis, oxidation). Novel reaction schemes were evaluated against an established PEG-maleimide system as a control. Hydrogel gelation times were evaluated via rheometry measurements. Successful crosslinking of the DBCO-azide (scheme 4 in FIG. 17) was achieved within the appropriate timeframe.

Example 2: Evaluation of Device Performance In Vitro

Figure 19:
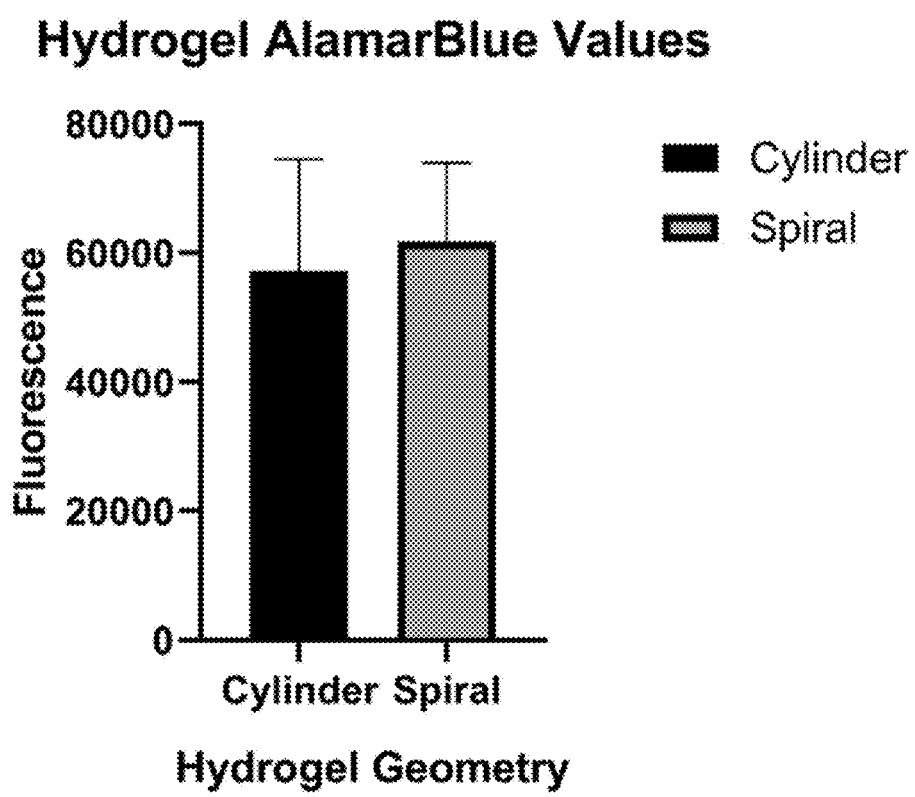
FIG. 19 shows cell viabilities in cylinder and spiral hydrogel geometries using hydrogel AlamarBlue values.

Optimal device designs were evaluated with continuous beta cell line INS-1 (single cells) in vitro for cell function and viability. Predictive device design may result in optimal short- and long-term function in vivo. FIG. 19 shows cell viabilities (AlamarBlue values) in cylinder and spiral (2 mm diameter) hydrogel geometries after 24 hours using an alginate hydrogel. This shows that the cells were viable in both macroencapsulation device geometries, indicating that injection molding within the injection mold device does not impart undue strain or stress on encapsulated cells.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A hydrogel macroencapsulation device comprising:
a biocompatible hydrogel operable to be crosslinked within an injection mold; and
a plurality of cells encapsulated within the hydrogel,
wherein the hydrogel macroencapsulation device is formed from the injection mold,
wherein the biocompatible hydrogel is multi-arm PEG functionalized with bioorthogonal reactive groups;
wherein the hydrogel macroencapsulation device has a three-dimensional geometry comprising a spiral, rounded, or cylindrical shape such that the plurality of cells encapsulated in the hydrogel are within 100 µm to 3000 µm from the edge of the hydrogel;
wherein the injection mold comprises a top portion and a bottom portion, the top portion and the bottom portion each comprising a portion of at least one channel operable to form the three-dimensional geometry of the hydrogel macroencapsulation device;
wherein the hydrogel macroencapsulation device has a length; and
wherein all edges of the hydrogel macroencapsulation device along the length are curved or rounded;
wherein the bioorthogonal reactive groups are selected from the group consisting of (E)-cyclooct-4-enol, dibenzocyclooctyne, azidodibenzocyclooctyne, dibenzoazacyclooctyne, difluorocyclooctyne 2, difluorocyclooctyne 3, bicyclononyne, and iodoacetamide.

2. The hydrogel macroencapsulation device of claim 1, wherein the hydrogel crosslinks within 1-60 minutes.

3. The hydrogel macroencapsulation device of claim 1, wherein the plurality of cells comprises islets.

4. The hydrogel macroencapsulation device of claim 3, wherein the hydrogel macroencapsulation device has a cell density of about 1 islet equivalent (IEQ)/µL to about 50 IEQ/µL.

5. The hydrogel macroencapsulation device of claim 3, wherein the hydrogel macroencapsulation device has a cell density of about 30 IEQ/µL to about 40 IEQ/µL.

6. The hydrogel macroencapsulation device of claim 3, wherein the hydrogel macroencapsulation device has a cell density of about 40 IEQ/µL to about 50 IEQ/µL.

7. The hydrogel macroencapsulation device of claim 3, wherein the hydrogel macroencapsulation device includes up to 100,000 IEQ cells.

8. The hydrogel macroencapsulation device of claim 1, wherein the three-dimensional geometry of the hydrogel macroencapsulation device is a spiral shape.

9. The hydrogel macroencapsulation device of claim 8, wherein the hydrogel macroencapsulation device covers an area having a length of about 6 cm to about 10 cm and a width of about 6 cm to about 10 cm.

10. The hydrogel macroencapsulation device of claim 1, wherein the hydrogel macroencapsulation device has a height of about 1 mm to about 3 cm.

11. The hydrogel macroencapsulation device of claim 1, wherein the hydrogel microencapsulation device has a diameter of about 100 µm to about 3000 µm.

* * * * *